US011803065B1

(12) United States Patent
Abou Shousha et al.

(10) Patent No.: US 11,803,065 B1
(45) Date of Patent: Oct. 31, 2023

(54) HEAD-MOUNTED DISPLAY ATTACHMENT DEVICE

(71) Applicant: Heru Inc., Miami, FL (US)

(72) Inventors: Mohamed Abou Shousha, Fort Lauderdale, FL (US); Michael Chen, Miami, FL (US); Rashed Kashem, Miramar, FL (US); Ece Turhal, Miami, FL (US); Dawn Smith, Miami, FL (US); Tom Nuzzo, Miami, FL (US); Keith Brock, Miami, FL (US); Collins Opoku-Baah, Miami, FL (US); Mary Durbin, Miami, FL (US); Alexander Jacob Miller, Miami, FL (US); Keith ÓHara, Miami, FL (US)

(73) Assignee: Heru Inc., Miami, FL (US)

( * ) Notice: Subject to any disclaimer, the term of this patent is extended or adjusted under 35 U.S.C. 154(b) by 0 days.

(21) Appl. No.: 17/936,235

(22) Filed: Sep. 28, 2022

(51) Int. Cl.
  *G09G 5/00* (2006.01)
  *G02B 27/01* (2006.01)
  *A61B 5/16* (2006.01)

(52) U.S. Cl.
  CPC ......... *G02B 27/0176* (2013.01); *A61B 5/163* (2017.08); *G02B 27/0172* (2013.01); *G02B 2027/0138* (2013.01)

(58) Field of Classification Search
  CPC .. G02B 27/0176; G02B 27/0172; A61B 5/163

USPC ............................................................ 345/8
See application file for complete search history.

(56) References Cited

U.S. PATENT DOCUMENTS

| | | | |
|---|---|---|---|
| 2018/0239151 A1* | 8/2018 | Chang | G02B 27/017 |
| 2018/0348812 A1* | 12/2018 | Miller | G06F 1/1686 |
| 2019/0104650 A1* | 4/2019 | Mcginty | G06F 1/1637 |
| 2020/0093362 A1* | 3/2020 | Jackson | G02B 27/0176 |
| 2020/0154098 A1* | 5/2020 | Ko | H04N 13/398 |
| 2020/0211207 A1* | 7/2020 | Chen | G06T 7/292 |
| 2021/0365064 A1* | 11/2021 | Liu | G06T 19/006 |

* cited by examiner

*Primary Examiner* — Jonathan M Blancha
(74) *Attorney, Agent, or Firm* — Perkins Coie LLP

(57) ABSTRACT

A head-mounted display and accessory system in which the accessory emits bleaching light through the head-mounted display to bleach photoreceptors for dark adaptation testing includes a casing, where a lens of a head-mounted display is positioned inside the cavity, and where an aperture of the casing is aligned with an exterior-facing camera of the head-mounted display. The system also includes an attachment body, where a posterior end of the attachment body is fixed to an anterior end of the casing, and where the attachment body includes a set of light-emitting diodes (LEDs), where the set of LEDs is attached to the posterior end of the attachment body and is directed towards the lens. The system also includes a circuitry that is configured to control light emission of the set of LEDs.

20 Claims, 6 Drawing Sheets

HEAD-MOUNTED DISPLAY ATTACHMENT DEVICE

BACKGROUND

Head-mounted displays are useful for various types of health-related testing, such as dark adaptation testing and another eye-related testing. Such testing provides data that is useful for determining eye-related conditions. During a dark adaptation test, photoreceptors of an eye are stimulated through one or more cycles of exposing an eye to darkened or illuminated conditions. The readings acquired during such a test may be used to diagnose eye-related information (e.g., age-related macular degeneration) and other types of health information, such as blood glucose.

SUMMARY

A head-mounted display (HMD) device may measure eye responses during a dark adaptation test or other tests that involve exposing an eye to different stimuli. Measured physiological changes may be paired with user-provided inputs that indicate when a user has detected a target stimulus. Despite the advantages that an HMD can provide to eye-related testing, however, hardware limitations prevent typical HMDs from being used for certain types of tests, such as dark adaptation testing. For example, because general-purpose HMDs are designed for eye comfort over-long user sessions, these HMDs are not configured to provide the intensity of light needed to bleach retinas as required during dark adaptation testing. Furthermore, while bleaching light is a necessary component of many tests, conventional tests may fail to account for user errors or program errors that may over-expose a user to bleaching light. Such overexposure may lead to discomfort and long-term eye damage. In addition, attachments to an HMD may cover up one or more HMD cameras, inhibiting positioning operations reliant on visual data provided by the HMD cameras.

Some embodiments may overcome this technical problem by using a dark adaptation accessory configured to be attached to an HMD (e.g., a wearable dark adaptation attachment configured to be mounted over one or more transparent lenses of the HMD). The accessory device may be capable of exposing an eye to bleaching light while being compatible with a head-mounted display capable of displaying stimuli and measuring eye-related information. The accessory device may include a light shield casing shaped to encompass at least the lenses of a head-mounted display, where the light shield casing is designed to shield light from the HMD when both the HMD and the dark adaptation accessory device are properly worn. The dark adaptation accessory device may also include an attachment body fixed to the front end of the light shield casing, where the attachment body includes various electronic equipment to perform bleaching operations. The attachment body may include a set of light-emitting diodes (LEDs) to emit light at a bleaching intensity. In some embodiments, the set of LEDs is directed towards the anterior end of the light shield casing. Light emission by the set of LEDs may be visible through the lenses of an HMD. In addition, the light shield casing may include a set of apertures through which cameras or microphones of the HMD may continue to collect data.

The attachment body may also include circuitry that is at least partially enclosed within the attachment body, where the circuitry may include integrated circuits, microprocessors, microcontrollers, etc. The circuitry may include controller circuitry in electrical communication with the set of LEDs that is configured to control the light emission of the set of LEDs. The circuitry may also include safety circuitry in electrical communication with the set of LEDs to deactivate the set of light-emitting diodes independently of the controller circuitry. Independent safety circuitry for the set of LEDs, may reduce the possibility of user error or program errors exposing a user to a damaging amount of bleaching light.

Various other aspects, features, and advantages of the invention will be apparent through the detailed description of the invention and the drawings attached hereto. It is also to be understood that both the foregoing general description and the following detailed description are examples, and not restrictive of the scope of the invention. As used in the specification and in the claims, the singular forms of "a," "an," and "the" include plural referents unless the context clearly dictates otherwise. In addition, as used in the specification and in the claims, the term "or" means "and/or" unless the context clearly dictates otherwise. Additionally, as used in the specification, "a portion" refers to a part of, or the entirety of (i.e., the entire portion), a given item (e.g., data) unless the context clearly dictates otherwise. Furthermore, a "set" may refer to a singular form or a plural form, such as that a "set of items" may refer to one item or a plurality of items.

BRIEF DESCRIPTION OF THE DRAWINGS

The accompanying drawings, which are incorporated in and form a part of this specification, illustrate embodiments of the invention and, together with the description, serve to explain the principles of the invention.

DETAILED DESCRIPTION

In the following description, for the purposes of explanation, numerous specific details are set forth in order to provide a thorough understanding of the embodiments of the invention. It will be appreciated, however, by those having skill in the art, that the embodiments of the invention may be practiced without these specific details or with an equivalent arrangement. In other cases, well-known structures and devices are shown in block diagram form in order to avoid unnecessarily obscuring the embodiments of the invention.

A head-mounted display (HMD) is a versatile device capable of performing various types of virtual reality or augmented reality operations. These HMDs permit a user to test a subject's health by exposing the subject to various visual or auditory stimuli and collecting readings of the subject's response to the visual or auditory stimuli in the form of eye-related readings. Such readings may provide valuable information, such as blood glucose amount, bleaching recovery time, etc. This information may then be used to diagnose health conditions, such as diabetes, glaucoma, or age-related macular degeneration.

In many cases, the visual stimuli that an HMD may emit may be limited with respect to color or brightness. For example, an HMD may be incapable of emitting bleaching light that would adequately bleach the rhodopsin of an eye. Without being capable of providing such bleaching light, typical systems may produce inaccurate results or require the use of room-scale bleaching equipment. Furthermore, in the case of an HMD that includes one or more transparent lenses, ambient light or light from other light sources may pollute or otherwise invalidate eye-related readings made by the HMD.

To overcome such challenges or other challenges, some embodiments may augment an HMD with an attachment device to shield a subject's eye from undesirable light and further expose the eye to bleaching light. It should be noted that the attachment device may be referred to as an attachment, accessory, or accessory device in some instances, and that these terms are non-limiting with respect to any relationship to an HMD. In some embodiments, an attachment device for an HMD may preserve the environmental awareness capabilities provided by an HMD by including a series of apertures that permit HMD sensors to continue acquiring data from its environment. For example, the attachment device may include a set of apertures that permit cameras on an HMD to continue collecting visual data and another set of apertures that permit microphones on the HMD to continue collecting auditory data from the HMD's environment. In addition, by including an attachment device to emit bleaching light, the attachment device may include additional safety circuitry that will protect a subject's eye from over-long bleaching light.

Figure 1A:
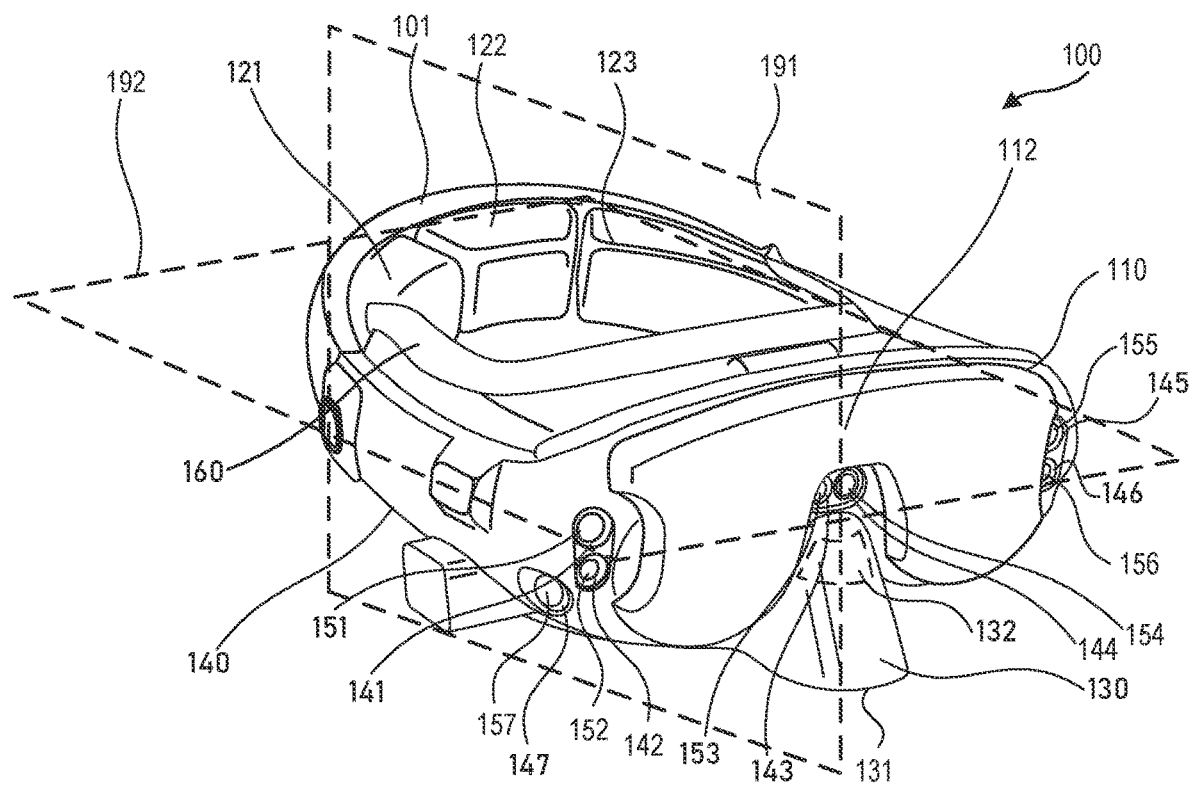
FIG. 1A is a first view of an example head-mounted display (HMD) and accessory system, in accordance with one or more embodiments.

FIG. 1A is a first view of an example head-mounted display (HMD) and accessory system, in accordance with one or more embodiments. The HMD and accessory system 100 includes an HMD 101, a light shield casing 140, an attachment body 110 that is fixed to the light shield casing 140. The HMD and accessory system 100 is bisected into a left section and right section by the sagittal plane 191 and may be separated into an upper and lower portion by the transverse plane 192. While the attachment body 110 is shown as an accessory body to the HMD 101 and may be disconnected from the HMD 101, some embodiments may integrate the attachment body 110 with the HMD 101 such that the attachment body 110 may be completely integrated with the HMD 101.

The HMD 101 includes a foam member 121, where the foam member 121 may be used to cushion a head as the light shield casing 140 is worn by the head. The HMD 101 may include a set of cameras usable for capturing visual information, a set of microphones to capture audio information, an orientation sensor to capture an orientation of the device with respect to a floor, etc. The set of cameras of the HMD 101 may include exterior-facing cameras 151-154 to capture visual information of an environment surrounding the HMD 101. The set of cameras of the HMD 101 may also include interior-facing cameras to capture eye-related information, such as a position or orientation of an eye. The HMD 101 may include additional cameras that are not shown in FIG. 1A or FIG. 1B. In some embodiments, the set of exterior-facing cameras of an HMD may be adjacent to a transparent lens of the HMD. Furthermore, as used in this disclosure, cameras may be on opposite sides of the transparent lenses by being symmetric to each other about the sagittal plane 191. For example, the exterior-facing camera 151 may be opposite of the transparent lens with respect to the exterior-facing camera 154.

Figure 1B:
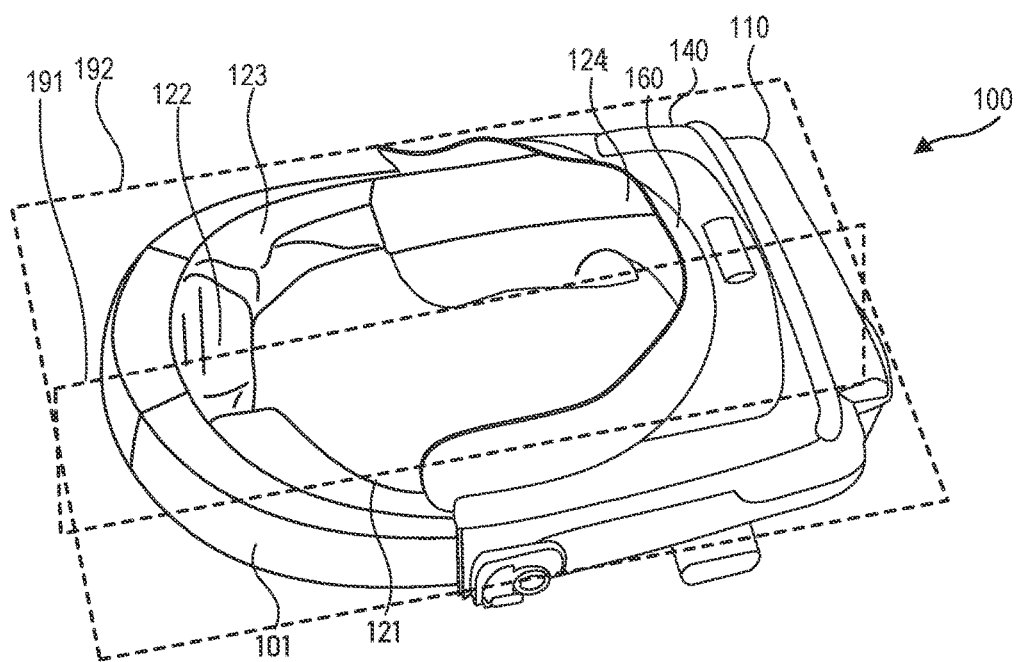
FIG. 1B is a second view of the example HMD and accessory system, in accordance with one or more embodiments.

As shown in FIG. 1B, the light shield casing 140 includes a cavity 124. When a subject's head wears the HMD and accessory system 100, a subject's face may cover the cavity 124 such that light is shielded from the cavity 124. In some embodiments, lenses of an HMD may be positioned inside of the cavity 124 such that light from external light sources is blocked from the inside of the cavity 124 and does not penetrate the lenses of the HMD. The light shield casing 140 may shield light from the cavity by forming a seal against light using a lip 160 of the light shield casing 140, where the lip 160 may be constructed from a flexible material, such as a flexible polymer. As used in this disclosure, a light source may include a direct source of light, such as the sun, a light bulb, a light-emitting diode (LED), etc. A light source may also include an indirect source of light, such as a mirror or a reflection off a surface.

The light shield casing 140 includes a plurality of apertures 141-144 and may include additional apertures not shown in FIG. 1A or FIG. 1B. The plurality of apertures 141-144 may be aligned with the light shield casing 140 such that the exterior-facing cameras 151-154 of the HMD 101 may capture images or other types of information through the apertures 141-144. As used in this disclosure, an aperture may be considered to be aligned with a camera when the camera is capable of acquiring images or other visual data through the aperture. Furthermore, an aperture may be aligned with multiple cameras if the aperture is sufficiently large such that the multiple cameras may each capture visual information through the aperture. For example, the apertures 142-143 may be replaced by a single aperture such that the exterior-facing cameras 152-153 are aligned with the single aperture. Furthermore, while not displayed, the light shield casing 140 may include a second microphone aperture that is symmetric to the microphone aperture 182 about the sagittal plane 191. Furthermore, the light shield casing 140 may include a microphone aperture 182, where a microphone 183 of the HMD 101 may record sound from the surrounding environment of the HMD 101. In addition, while the light shield casing may be described with three apertures, a light shield casing having other numbers or configurations of apertures is possible. For example, a light shield casing may include one aperture, two apertures, three apertures, a number of apertures greater than three apertures, some other number of apertures, etc. For example, the plurality of apertures of a light shield may include at least six apertures, where at least one of the six apertures may be configured to align with a microphone or other audio recording device.

When the light shield casing 140 is positioned to encompass an HMD, the holes 141-144 may permit cameras of the HMD to capture surrounding visual information or other information while still blocking light from one or more lenses of the HMD. By permitting the cameras, microphones, or other sensors of an HMD to remain functional while the HMD is surrounded by the light shield casing 140, an HMD may be capable of performing operations that rely on data from the sensors while still shielding a wearer's eyes from unwanted light. In some embodiments, the HMD and accessory system 100 may be used as a dark adaptation testing device. For example, the HMD 101 may collect visual information via the exterior-facing cameras 151-154 while partially within the light shield casing 140 to determine a position of the HMD 101 during a dark adaptation test without influencing the light perceived by a wearer of the HMD 101.

The attachment body 110 is fixed to an anterior end (i.e., front end) of the light shield casing 140 such that the posterior end (i.e., back end) of the attachment body 110 is facing towards the cavity 124. When the light shield casing 140 is then fitted over an HMD, an LED of the attachment body 110 may emit light. The light may pass through a lens of the HMD and be visible to an eye. In some embodiments, the attachment body 110 may be detachable from the light shield casing 140. Alternatively, the attachment body 110 may be permanently fixed to the light shield casing 140. In some embodiments, the anterior end of the light shield casing 140 may be formed such that light is shielded from cavities formed by the light shield casing 140 without requiring that the attachment body 110 is attached to the light shield casing 140.

The attachment body 110 includes a midsection 112, where the midsection 112 is positioned above a nose protrusion 130 of the light shield casing 140. The midsection 112 may be thinner along a vertical axis of the attachment body 110 in comparison to a left section or a right section of the attachment body 110. The nose protrusion 130 may include an opening 131 in the bottom direction of the HMD and accessory system 100, where a human nose may fit inside the nose protrusion 130. In some embodiments, the nose protrusion 130 may include a non-rigid member 132, such as a foam member or an elastic member. The non-rigid member 132 may prevent light from reaching the cavity 124 via the opening 131.

While the attachment body 110 and the light shield casing 140 are shown to be symmetric with respect to the sagittal plane 191, other embodiments are possible. For example, some embodiments may include a set of apertures on a left section of the light shield casing 140 while not having apertures on a right section of the light shield casing 140. Alternatively, some embodiments may include an attachment body that is asymmetric in shape or may be fixed to a light shield casing in an asymmetric manner.

In some embodiments, the attachment body 110 and the light shield casing 140 may be physically separate components. Alternatively, in some embodiments, an attachment body and a light shield casing may be part of a unibody construction or may be otherwise fused together. Furthermore, while the lip 160 may be a flexible polymer in some embodiments, the lip 160 may include alternative materials or include additional materials in other embodiments. For example, the lip 160 may be made of or otherwise include a foam cushion, a rigid material, etc.

Figure 2:
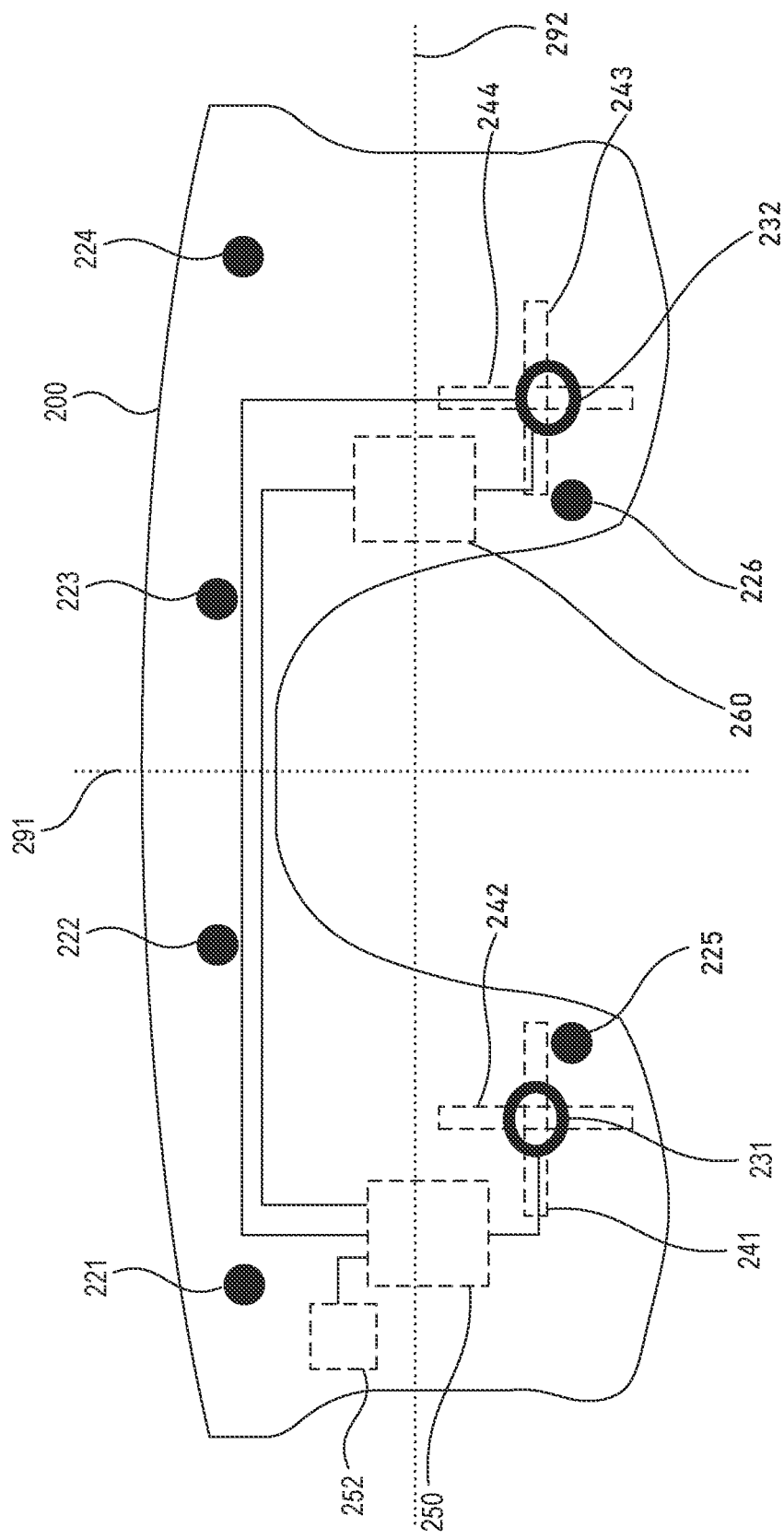
FIG. 2 is a diagram of an attachment body of an attachment device, in accordance with one or more embodiments.

FIG. 2 is a diagram of an attachment body of an attachment device, in accordance with one or more embodiments. The posterior end of the attachment body 200 is shown with attachment members 221-226, where attachment members 221-226 may fix the attachment body to a light shield casing at a plurality of attachment positions. As used in this disclosure, an attachment member may include any item or combination of items used to attach one object with another object at their respective attachment positions. An attachment member may include threaded members, such as screws, bolts, nuts, male coupling members, female coupling members, etc. Furthermore, some embodiments may use more than one type of attachment members. For example, the attachment members 221-224 may include screws, and the attachment members 225-226 may include bolts. Various other types of coupling mechanisms or materials may be used. For example, the attachment members 221-226 may include snap fastener members, adhesive materials, solder, other metals, etc.

The attachment body 200 may include a first LED 231 and a second LED 232. The attachment body 200 may also at least partially enclose controller circuitry 250, where the controller circuitry 250 is in electrical communication with the LEDs 231-232. The controller circuitry 250 may include an integrated circuit, a microprocessor, a microcontroller, or other circuitry to control the operations of the LEDs 231-232. The attachment body 200 may also include an interface 252, where the computing devices may send commands to and receive data from the controller circuitry 250 via the interface 252. For example, the interface 252 may include a wireless network antenna such that the controller circuitry may receive commands to activate or deactivate the LEDs 231-232 via wireless messages received by the interface 252. The first and second LEDs may be positioned at a posterior end of the attachment body 200, where the posterior end of the attachment body 200 may be fixed to an anterior end of a light shield casing.

The first LED 231 and second LED 232 may each be part of a panel of LEDs or another collection of LEDs. For example, the first LED 231 may be surrounded by other LEDs to form a first set of LEDs. The second LED 232 may be surrounded by other LEDs to form a second set of LEDs. The first LED 231 and second LED 232 may be substantially symmetric with respect to a sagittal plane 291 of the attachment body 200. As used in this disclosure, a first item may be substantially symmetric to a second item with respect to a point, line, or plane if the distance from an edge of the first item to the point, line, or plane is within 25% of the distance from an edge of the second item to the point, line, or plane. In some embodiments, the distance between the first LED 231 and the second LED 232 may be determined based on an approximation of the distance between two retinas. For a human head, the distance between the first LED 231 and second LED 232 may be a distance greater than or equal to 40 millimeters (mm), greater than 50 mm, greater than 60 mm, or greater than some other value. For example, the distance between the first LED 231 and second LED 232 may be 45 mm, 50 mm, 55 mm, 60 mm, 62 mm, 65 mm, or some other value. Furthermore, the LEDs 231-232 may be configured to illuminate an eye to satisfy a size requirement of the illuminated region. For example, an LED may be configured to illuminate a region of the eye such that at least one arc of the illuminated region has an arc size that is greater than one degree, a value greater than one degree, two degrees, a value greater than two degrees, etc.

The first and second LEDs 231-232 are positioned at locations below a transverse plane 292 of the attachment body 200. The position of the first and second LEDs 231-232 may be advantageous for certain types of bleaching operations, such as bleaching operations that target the inferior visual meridian of an eye. While the first and second LEDs 231-232 are below the transverse plane 292, other embodiments may include an attachment body having one or more LEDs above a transverse plane of the attachment body. LEDs above the transverse plane of the attachment body may be more suitable for illuminating a superior visual meridian of an eye.

The attachment body 200 may also include safety circuitry 260, where the safety circuitry 260 may also be in electrical communication with the LEDs 231-232. In some embodiments, the safety circuitry 260 may be simpler than the controller circuitry 250 with respect to the number of circuitry components or the capabilities of the respective circuitry components. The safety circuitry 260 may act independently of the controller circuitry 250 and be configured to deactivate the LEDs 231-232 under certain conditions. In some embodiments, such conditions may be related to the overexposure to bleaching light. As used in this disclosure, a bleaching light is a light having a sufficient intensity to bleach the photoreceptors of an eye ("bleaching intensity") such that the vision of the eye is temporarily impaired or eliminated. For example, an LED may emit bleaching light by emitting with a light output that is greater than or equal to a bleaching threshold, where the bleaching threshold may be a value greater than 1000 lumens, such as 1200 lumens, 1300 lumens, 1400 lumens, etc.

The safety circuitry may include a set of relays to deactivate the LEDs 231-232 when a set of LEDs have emitted bleaching light for a duration threshold. Alternatively, or in addition, the safety circuitry may include a microcontroller that is configured to deactivate the set of LEDs based on a determination that the set of LEDs has emitted bleaching light for the duration threshold. The duration threshold may vary based on a test, patient biology, or other factors and may be greater than one second, greater than three seconds, greater than five seconds, greater than ten seconds, etc. For example, some embodiments may set the duration threshold to be equal to six seconds or some other duration less than ten seconds.

The safety circuitry 260 may inhibit overbleaching in various ways. In some embodiments, the safety circuitry 260 may be configured such that a power consumption of the LEDs may be used as a threshold to determine whether a bleaching light is being generated by the set of LEDs. For example, the safety circuitry 260 may be configured to deactivate the first LED 231 if the power consumption of the LED 231 exceeds a threshold and if the power consumption is maintained for a duration threshold. Such operations may be useful if the first LED 231 operates as a variable brightness LED capable of emitting both bleaching and non-bleaching light, where the brightness of the first LED 231 may depend on the amount of power provided to the first LED 231.

While the safety circuitry 260 is shown as a single unit that is in electrical communication with both the first LED 231 and the second LED 232, other embodiments may include multiple safety circuitries that are independent of each other and connected to different sets of LEDs. For example, an attachment body may include first safety circuitry that is connected to a first set of LEDs and a second safety circuitry that is connected to a second set of LEDs, where controller circuitry may be connected to and be capable of controlling both the first and second sets of LEDs.

Alternatively, the safety circuitry 260 may be configured to account for an LED that emits a bleaching light by default. For example, the first LED 231 may be constructed such that activation of the first LED 231 is sufficient to generate a bleaching light. The safety circuitry 260 may be configured to account for such types of LEDs by deactivating the first LED 231 based on a determination that the first LED 231 has current passing through the LED for a duration that is greater than a duration threshold. Furthermore, instead of measuring power directly, the safety circuitry may receive measurements from a brightness sensor that indicates whether the first LED 231 is emitting a bleaching light. Based on a set of readings provided by a brightness sensor indicating that the first LED 231 is emitting a bleaching light for a duration greater than a duration threshold, some embodiments may deactivate the first LED 231.

In some embodiments, one or more LEDs of an attachment body may be movable along one or more directions. For example, the first LED 231 may be slidable in a horizontal direction along a set of tracks 241 and may be slidable in a vertical direction along a set of tracks 242. Similarly, the second LED 232 may be slidable in a horizontal direction along a set of tracks 243 and may be slidable in a vertical direction along a set of tracks 244. In some embodiments, a movable LED may be moved directly, such as by applying force on an LED. Alternatively, some embodiments may include a lever or other mechanism to reconfigure the position of one or more LEDs of an attachment body.

Figure 3:
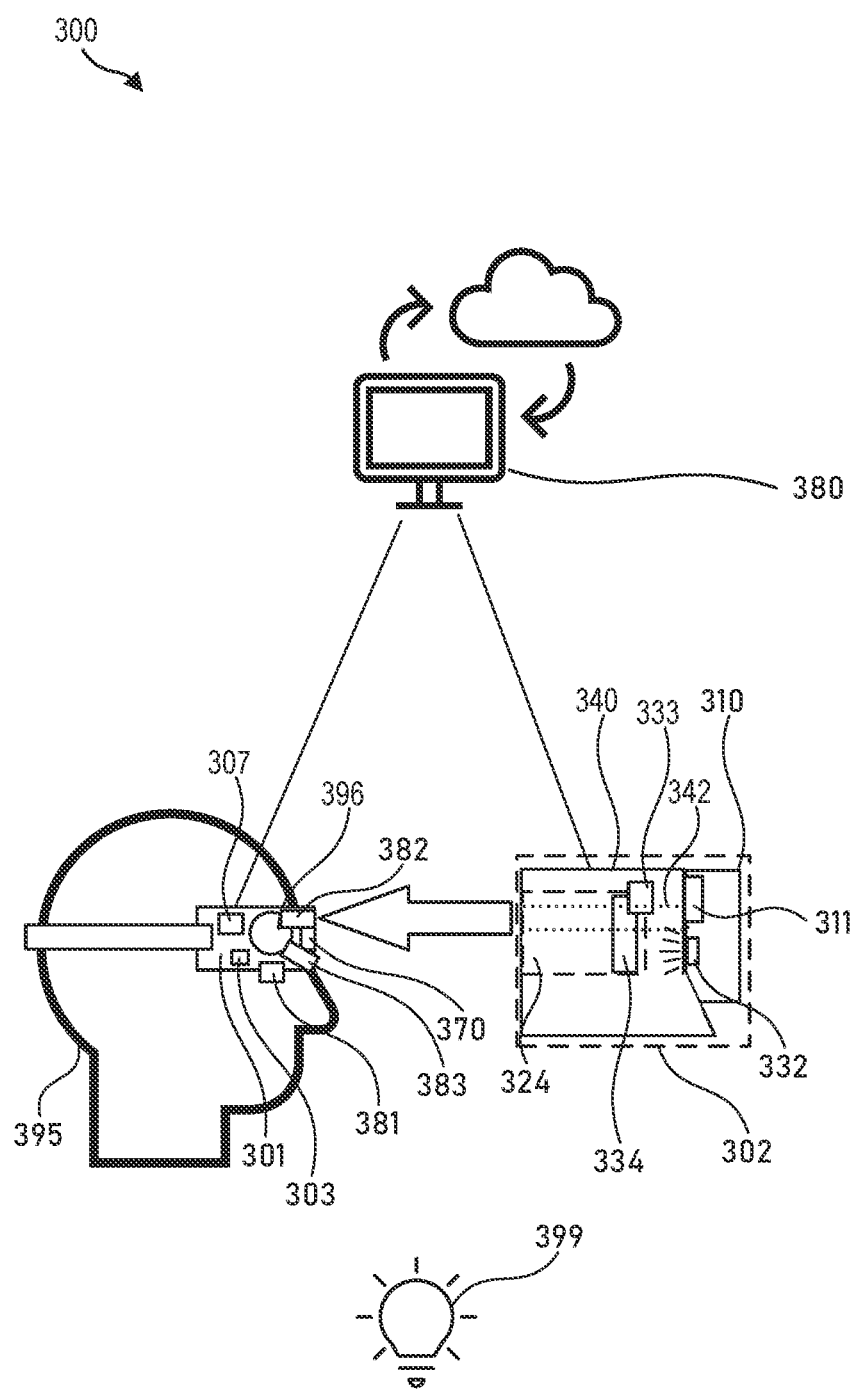
FIG. 3 depicts an HMD and accessory system being used in conjunction with a computer system, in accordance with one or more embodiments.

FIG. 3 depicts an HMD and accessory system being used in conjunction with a computer system, in accordance with one or more embodiments. A subject 395 may wear the HMD 301, which may include a computing device 307, where the computing device 307 may include a processor, microprocessor, controller, or other circuitry. In some embodiments, an eye 396 of the subject may be capable of viewing light provided by a light source 399 through lenses 370 of the HMD 301 when the lenses 370 is not within an accessory device 302, where the accessory device 302 may include a light shield casing 340 and an attachment body 310. The HMD 301 may include an interior-facing camera to capture eye-related information and a set of exterior-facing cameras that include an exterior-facing camera 382.

In some embodiments, the accessory device 302 may be placed over the HMD 301. The light shield casing 340 may include a cavity 324 that may encompass a portion of the HMD 301 such that the lenses 370 are within the cavity 324. In addition, the light shield casing 340 may include a neutral density filter 334. The neutral density filter 334 may be fixed to the shield casing 340 via a filter coupling 333.

Once the light shield casing 340 is positioned over the HMD 301, light from the light source 399 may be shielded from the lenses 370 by the light shield casing 340. However, an aperture 342 may permit the exterior-facing camera 382 to continue capturing visual information from the surroundings. For example, the exterior-facing camera 382 may continue to read light information from the light source 399 via light passing from the exterior through the aperture 342.

The attachment body 310 includes an LED 332, where the LED 332 may emit a bleaching light, where a bleaching light may be a light with a spectrum and illuminance such that a retina is bleached. For example, the LED 332 may emit a bleaching light having a wavelength of or set wavelengths within the visible spectrum for a human eye (i.e., a wavelength between 380 nm to 700 nm). Various types of wavelength spectrums may be used as bleaching light. For example, a bleaching light may include light having a spectrum centered around 550 nm that is greater than a bleaching threshold. A bleaching threshold may represent a threshold luminosity such that light having a luminosity greater than the threshold may be considered a bleaching light that is sufficient to bleach photoreceptors. For example, a bleaching light may have a luminosity equal to $1.0 \times 10^1 \backslash 4$ cd/s.m^2, greater than $1.0 \times 10^4$ cd/s.m^2, equal to $1.0 \times 10^5$ cd/s.m^2, greater than $1.0 \times 10^5$ cd/s.m^2, or some other value, such as $1.8 \times 10^4$ cd/s.m^2.

In some embodiments, a user may initiate an eye-related test using a computing system 380 that is in communication with the HMD 301 and the attachment device that includes the attachment body 310 and the light shield casing 340. The computing system 380 may include a standalone computer capable of operating without connecting to another computing device outside of a local network. Alternatively, or in addition, the computing system 380 may include a computing system that receives program instructions or required data from an external data source not available through a local network.

In some embodiments, the computing system 380 may initiate operations to perform dark adaptation testing or another eye-related test. The computing system 380 may communicate with the HMD 301 via a wireless connection or wired connection. For example, the computing system 380 may send a wireless message to the computing device 307 to initiate a dark adaptation test or another visual test. Similarly, the computing system 380 may communicate with the light shield casing 340 or the attachment body 310 via a wired or wireless connection. For example, the computing system 380 may send a command to the attachment body 310 via a Bluetooth® connection, where the command may cause the attachment body 310 to activate the LED 332.

In some embodiments, the computing system 380 may communicate with both the HMD 301 and the attachment body 310 to perform one or more operations. For example, the HMD 301 may present an initial set of instructions to a subject 395 and request a response from the subject 395. After the subject 395 provides a requested response (e.g., pressing a button, making a statement, etc.), the computing system 380 may send a first set of instructions to the HMD 301 to calibrate readings to more accurately measure eye-related data associated with the eye 396. After the HMD 301 sends a message to the computing system 380 that calibration operations have been completed, the computing system 380 may send instructions to the attachment body 310 to emit a bleaching light. The computing system 380 may determine the position of a fixation point based on eye-related readings and a known position of the LED 332, and send a message to the HMD 301 that causes the HMD 301 to display a visual stimulus at the fixation point on the lenses 370. After receiving a message from the HMD 301 that the eye 396 has set its gaze at the fixation point, the computing system 380 may send a message to the attachment body 310 that causes the attachment body 310 to emit a bleaching light using the LED 332.

In some embodiments, an application executed by the computing device 307 of the HMD 301 may be used to control operations of components of the attachment body 310 or other electronic components. For example, the application executed by computing device 307 may begin a visual test program and send a wireless message to a circuitry of the attachment body 310 to activate the LED 332 by using a wireless headset communication subsystem 303. The wireless message may be based on one of various types of communication standards, such as a Bluetooth standard, a Wi-Fi Direct standard, a near field communication (NFC) standard, a ZigBee® standard, a 6LoWPAN standard, etc.

In some embodiments, an application being executed by the computing device 307 may retrieve data from the interior-facing camera 383 and send instructions to control the LED 332 based on this data. For example, the computing device 307 may execute an application to perform a Viola-Jones object detection framework to detect an eye in a set of images using a boosted feature classifier based on video data provided by the interior-facing camera 383. In some embodiments, the application may determine a size associated with the eye and whether this size satisfies a minimum threshold. For example, the computing device 307 may use a set of classifiers to detect a pupil size based on images collected by the interior-facing camera 383 and determine whether the pupil size satisfies a threshold. In response to a determination that the pupil size satisfies the threshold, the computing device 307 may activate the LED 332 by sending a wireless message via the wireless headset communication subsystem 303 to the attachment body 310. After receiving the wireless message from the computing device 307, a circuitry 311 of the attachment body 310 may activate the LED 332 based on parameters of the wireless message. Furthermore, the application executed by the computing device 307 may permit additional sensor data to trigger the activation of the LED 332, such as by receiving voice instructions captured from a microphone 381, motion detected by the exterior-facing camera 382, feeling a set of touches on the body of the HMD 301, etc.

In some embodiments, the computing device 307 may modify instructions to the LED 332 based on the detected pupil size. For example, the computing device 307 may reduce the intensity of the light emitted by the LED 332 in response to detecting greater pupil sizes. For example, the computing device 307 may send a first message to the attachment body 310 that causes the LED 332 to luminesce with a greater intensity when a pupil size is less than 4 mm and cause the LED 332 to luminesce with a lesser intensity when the pupil size is greater than 4 mm. Furthermore, some embodiments may determine that a pupil is insufficiently bleached based on data provided by the interior-facing camera 383 and extend an emission duration of the LED 332. Alternatively, or additionally, the LED 332 may be part of an LED panel, such that a greater number of LEDs may be activated for smaller pupil sizes. Furthermore, some embodiments may use a function that indicates a negative correlation between a pupil size and an amount of light from the LED 332 or an LED panel comprising the LED 332. For example, some embodiments may use a function "$L = (K_1 - r) * K_2$," where L is a luminosity, "$K_1$" is a first constant, "r" is a retina size, and "$K_2$" is a second constant. Some embodiments may dynamically determine an electrical current used to activate the LED 332 or a total number of LEDs to activate for a bleaching operation based on the computed luminosity "L."

In some embodiments, a testing application executed by the computing device 307 may detect that the gaze location of the subject 395 is focused on a target user interface (UI) element or looking in a target direction based on data collected by the interior-facing camera 383. In response, the application may send instructions to the attachment body 310 to activate the LED 332. For example, the HMD 301 may display a set of instructions that causes the subject 395 to look at a target UI location. In some embodiments, the target UI location may be represented by a target region associated with a target UI location, such that a gaze location determined to be within the target region is considered to be focused at the target UI location. In response to a determination that the gaze location of the eye 396 is focused on the target UI location based on images provided by the interior-facing camera 383, the application may activate the LED 332. Furthermore, the application may send another message to the attachment body 310 to turn off the LED 332 based on a determination that the target UI location is no longer a focus of the user's gaze. Alternatively, some embodiments may forego waiting for the subject 395 to focus on a particular UI location or a particular direction before activating the LED 332. Some embodiments may determine a gaze location or direction of the eye 396, determine a subset of a set of LEDs that are near the gaze location or direction, and activate this subset of LEDs to bleach or stimulate the eye 396.

Some embodiments may perform calibration operations to determine an LED intensity, a number of LEDs to activate, an activation duration, or another LED operational parameter. For example, some embodiments may obtain feedback from the subject 395 indicating that an LED intensity was too uncomfortable after an initial testing session. Based on the feedback, some embodiments may then adjust an amount of current passing through the LED 332 for the user during a later testing session by reducing the total current. Some embodiments may further combine the subject's feedback with other feedback to update a default set of parameters transmitted by the computing device 307 when activating the LED 332 for other subjects.

The application may then send a second message to the circuitry to deactivate the LED 332 after a pre-determined bleaching duration threshold is satisfied. Alternatively, or in addition, the application may be triggered by a user command (e.g., a button press, a voice command, etc.) or in response to sensor data (e.g., sensor data captured by the exterior-facing camera 382) to activate or deactivate the bleaching light. Furthermore, sensor data that captures an interior-facing camera 383 of the computing device 307 may cause the computing device 307 to send a message to the circuitry of the attachment body 310. For example, an application executed by the computing device 307 may determine that a user's eyes are closed or are not adequately bleached by based on a set of images captured by the interior-facing camera 383 and, in response, activate the LED 332 or extend duration of activation of the LED 332.

Figure 4:
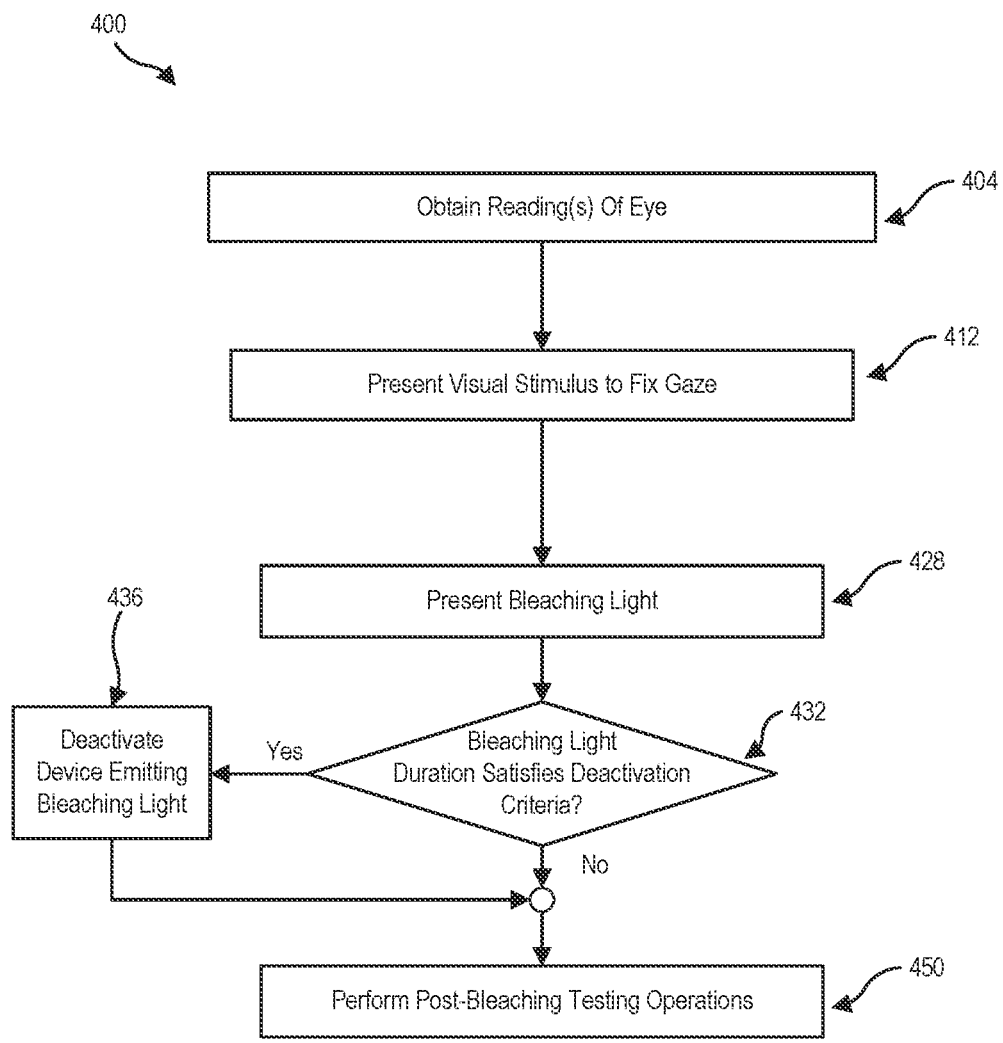
FIG. 4 is a flowchart of operations to perform dark adaptation testing using an accessory device, in accordance with one or more embodiments.

FIG. 4 is a flowchart of operations to perform dark adaptation testing using an accessory device, in accordance with one or more embodiments. Some embodiments may obtain a set of readings of an eye, as indicated by block 404. Various types of eye-related readings may be collected from an eye using one or more sensors. Eye-related readings may include images of an eye, colors of an eye, brightness of a section of an eye, or other information that may be captured by a camera or another type of sensor. Furthermore, such readings may be processed to determine other types of eye-related information, such as measurements of a pupil size or another size of one or more features of an eye, the color of one or more features of an eye, the orientation of an eye, etc. For example, some embodiments may collect eye-related readings and process the eye-related readings to determine eye-related information such as the angle of an eye with respect to the focal point of the eye and a reference direction, such as a horizontal or vertical direction. Other eye-related readings may include a retina infrared light reflection measurements, other light reflection measurements, motion sensor readings, etc. As described elsewhere in this disclosure, some embodiments may determine the position of an eye with respect to an illuminating component, such as an LED. Some embodiments may continue to measure eye-related data throughout an operation. Furthermore, as described elsewhere in this disclosure, some embodiments may adjust one or more parameters of the operation in response to the measurements.

In some embodiments, the sensors used to measure eye-related data may be attached to an HMD. For example, the HMD may include a set of interior-facing cameras to measure eye responses to stimuli. Alternatively, or in addition, the sensors used to measure eye-related data may be attached to a light shield casing or attachment body. For example, a light shield casing that encloses a portion of an HMD may include an infrared camera or another type of sensor to measure eye-related information.

Some embodiments may present a visual stimulus to fix a gaze, as indicated by block 412. Some embodiments may present a visual stimulus over the course of an examination operation. For example, some embodiments may present a circular shape that is one degree in diameter at a determined fixation position.

Some embodiments may determine the position of a visual stimulus designed for fixation based on the eye-related readings described for block 404. For example, some embodiments may use the eye-related readings to determine a fixation position that would cause an eye fixated at the fixation position to be a preset number of degrees from an LED or within a preset range from the LED. The preset number of degrees or preset range may vary based on a specific application or type of operation. For example, some embodiments may determine a fixation position such that the visual stimulus location is six degrees above a bleaching location. In such a configuration, a bleaching LED may provide a bleaching light that is centered at six degrees on the inferior visual meridian of an eye. Some embodiments may then display a visual stimulus at the fixation position on the lens of an HMD or may otherwise present the visual stimulus on a surface that may be viewed through the lens of the HMD.

Some embodiments may generate a warning if a sensor detects that the eye has gone beyond a threshold with respect to the angular distance between its fixated gaze and a fixation point. For example, some embodiments may determine that an eye has shifted its focus away from a fixation point by more than 30% based on sensor measurements acquired from sensors of an HMD and, in response, present a warning using the HMD.

Some embodiments may adjust a stimulus brightness based on measurements while the stimulus is being presented. For example, some embodiments may continuously measure a pupil radius. Some embodiments may then determine a new stimulus brightness by multiplying a preset brightness of the stimulus by a factor that is inversely proportional to a pupil radius or a function that is positively correlated with the pupil radius. For example, some embodiments may determine a brightness for a stimulus by multiplying a preset brightness by the value $2/x^2$, where "x" may be the value of a pupil radius in millimeters.

Some embodiments may present a bleaching light, as indicated by block 428. As described elsewhere in this disclosure, some embodiments may send a message to a device containing bleaching light, such as an attachment body that includes an LED capable of emitting a bleaching light. The attachment body may include controller circuitry that may cause the LED to emit the bleaching light and may further determine which subset of LEDs of a set of LEDs to activate. An LED may be caused to emit a bleaching light that is at least four degrees in diameter on the surface of a retina.

Some embodiments may combine the brightness of an HMD with the light emitted from an LED of an attachment body to generate a bleaching light. For example, some embodiments may display a first light on a lens using an HMD. Some embodiments may then activate an LED of an attachment body, where the light from the LED and the HMD may combine to form a bleaching light. For example, some embodiments may determine that an eye is fixated at a first position and further determine that an LED of an attachment body would illuminate at six degrees below a horizontal angle of an eye. In response, some embodiments may display a light using the HMD that is also six degrees below the horizontal angle of the eye such that the light from the LED and the light displayed by the HMD are aligned with respect to the center of an eye.

In some embodiments, the device used to provide bleaching light may include a plurality of LEDs capable of emitting bleaching light. Some embodiments may then determine which of the plurality of LEDs to activate to most effectively bleach a retina. For example, some embodiments may determine that a fixation position is at a specified location and, in response, select an LED that is at least six degrees below the fixation position. After activation, the selected LED may then emit bleaching light.

Some embodiments may determine whether a bleaching light duration satisfies a set of deactivation criteria, as indicated by block 432. In some embodiments, an attachment body used to emit bleaching light may include safety circuitry to prevent the dangerous durations of bleaching light. The safety circuitry or a computing device may include a set of deactivation criteria to prevent the emission of an unsafe amount of bleaching light by stopping the device from emitting the bleaching light. In some embodiments, satisfying a set of deactivation criteria may include satisfying a threshold, where the threshold may be a duration threshold, a power consumption threshold, etc. In many cases, a bleaching light may be deactivated if the device emits a bleaching light for longer than a duration threshold.

Some embodiments may use safety circuitry that is in electronic communication with the LED but operates independently of controller circuitry or other circuitry used to control the LED. The safety circuitry may include various types of electronic components such as relays or microcontrollers, where the electronic components may be configured to deactivate an LED. The electronic components of safety circuitry may be configured to determine that a bleaching light duration has exceeded a duration threshold in response to a determination that an LED has been provided at least a preset amount of power for at least the duration threshold. For example, some embodiments may use a microcontroller of the safety circuitry to determine whether a set of LEDs has consumed enough power to exceed a power threshold. The power threshold may be a value such as 0.001 Watts (W), a value greater than 0.001 W, 0.1 W, a value greater than 0.1 W, or some other value. In response to a determination that the set of LEDs has a power consumption that satisfies a power threshold (e.g., by being greater than the power threshold, by being greater than or equal to the power threshold, etc.), some embodiments may then determine the light emission duration of the set of LEDs satisfies a duration threshold (e.g., by being greater than the duration threshold, by being greater than or equal to the duration threshold, etc.). In some embodiments, the duration threshold may be 0.01 seconds, a value less than 0.01 seconds, one second, a value less than one second, five seconds, a value less than five seconds, six seconds, a value less than six seconds, ten seconds, a value less than ten seconds, etc.

In some embodiments, operations to determine whether a set of LEDs should be deactivated may be performed by other circuitry or a computer device that is separate from an attachment body. For example, an attachment device may include safety circuitry that deactivates an LED if the LED is used for longer than six seconds. A controller circuitry of the attachment device may retrieve instructions from a computer system that causes the controller circuitry to deactivate the LED if the LED is used for longer than one second.

In some embodiments, operations to determine whether a set of LEDs should be deactivated may include obtaining data from sensors of an HMD or another device that is physically separate from an attachment device. For example, an HMD may provide a retina size or a measured rhodopsin content to a computer system, where the computer system may then determine whether measurements provided by the HMD satisfy a set of deactivation criteria. If the computer system determines that the measurements provided by the HMD satisfy the set of deactivation criteria, the computer system may then send instructions to the circuitry of an attachment device to deactivate an LED of the attachment device. In response to a determination that the set of deactivation criteria has been satisfied, operations of the process 400 may proceed to block 436. Otherwise, operations of the process 400 may proceed to block 450.

Some embodiments may deactivate a device emitting a bleaching light, as indicated by block 436. As described elsewhere in this disclosure, an attachment device may include controller circuitry to control the activation or deactivation of an LED and may also include safety circuitry to deactivate the LED independently of commands sent by the control circuitry. Furthermore, some embodiments may send, to a computing device, an error message or other indication that the safety circuitry was activated to deactivate one or more LEDs. In addition, some embodiments may identify the stage of a multistage operation that requires multiple iterations of reaching light emission.

Some embodiments may perform post-bleaching testing operations, as indicated by block 450. As described elsewhere in this disclosure, a bleaching operation may be used as part of a dark adaptation test. After bleaching an eye, some embodiments may display a visual stimulus (e.g., a flashing light) and wait for a subject's response indicating that the subject's photoreceptors had sufficiently recovered to perceive the visual stimulus. Alternatively, some embodiments display a flashing and bleaching light concurrently. For example, some embodiments may concurrently display a flashing light on an HMD lens while also using an LED to emit bleaching light. After receiving the subject's response, some embodiments may record the duration between when an LED was prevented from displaying bleaching light and when the subject responded. Some embodiments may then determine whether the duration satisfies a recovery threshold, where a determination that the subject's required time to respond is greater than a recovery threshold may indicate an eye-related status or a health condition.

Figure 5:
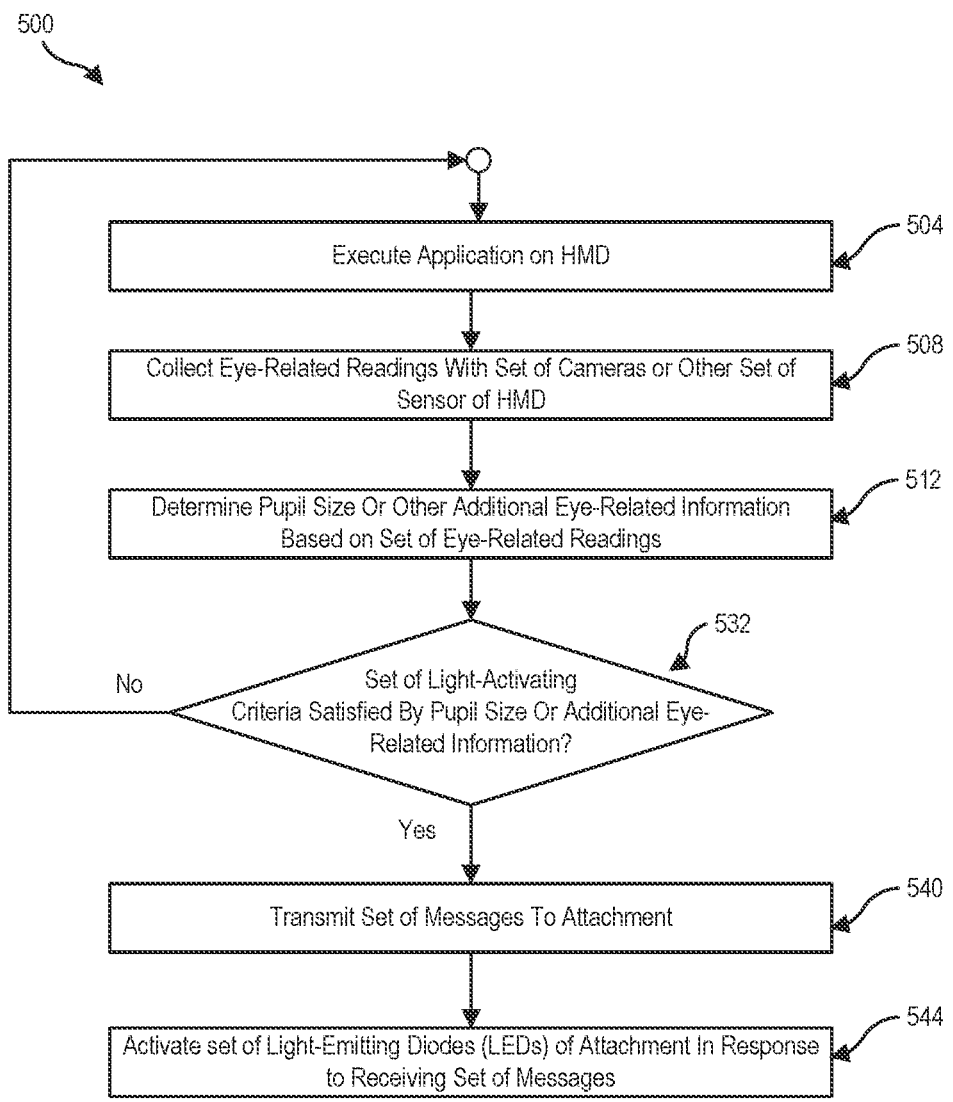
FIG. 5 is a flowchart of operations to perform testing with an HMD and accessory device system, in accordance with one or more embodiments.

FIG. 5 is a flowchart of operations to perform testing with an HMD and accessory device system, in accordance with one or more embodiments. Some embodiments may execute an application on an HMD, as indicated by block 504. The HMD may include a set of processors and the memory storing program code, where the set of processors may execute the program code to execute an application on the HMD. In some embodiments, the HMD may obtain the program code used to execute the application or a portion of the program code through an online platform. For example, a user may access an online platform and select an application to cause the HMD to download program code for the application via the online platform.

In some embodiments, operations performed by an HMD may be performed by multiple applications corresponding with different sets of program code. For example, as described elsewhere in this disclosure, some embodiments may capture images with a set of cameras using a first application and process the images with a second application to determine pupil sizes or other eye-related information. While some embodiments may be described as performing operations with a single application, it should be understood that any operation, combination of operations, or sub-operations of an operation may be performed by multiple applications. Furthermore, one or more operations that are described as being performed by an HMD may be performed by other computing devices, such as another mobile computing device in the proximity of the HMD, a remote computing device, etc.

In some embodiments, the HMD may be triggered by one or more stimuli to perform other operations described in this disclosure, such as the presentation of visual stimulus or the transmission of a message that causes bleaching light emission. For example, some embodiments may configure the HMD with an application that causes the HMD to perform one or more operations described in this disclosure based on visual stimulus captured by a set of exterior-facing sensors of the HMD. The visual stimulus may include images, brightness measurements, infrared measurements, etc. For example, an application executing on the HMD may perform operations to generate a set of values representing a target motion or a target shape based on a shape, motion types, or other information. Such information may be determined based on a set of images collected by an exterior-facing camera of the HMD. Some embodiments may then determine whether the target motion, target shape, or other information satisfies a set of visual stimulus criteria. In response to a determination that the set of visual stimulus criteria is satisfied, some embodiments may initiate a testing operation that causes the HMD to perform one or more operations described in this disclosure, such as operations to collect eye-related readings as described by block 508, operations to determine eye-related information as described by block 512, operations to determine whether a set of light-activating criteria is satisfied as described by block 532, etc.

Various types of applications, modules, services, etc. may be used to determine the presence of a specific shape, detect a type of motion, or perform other operations based on object recognition. For example, some embodiments may collect image data from an exterior-facing camera and provide the image data to a machine learning application that detects that a hand is present and may further determine a shape or orientation of the hand. After determining that the detected hand is controlled to present a specific hand signal, the application may cause the HMD to perform one or more operations described in this disclosure. For example, some embodiments may send a message to an accessory that causes the accessory to emit a bleaching light in response to detecting the hand signal. Alternatively, or additionally, some embodiments may capture images from exterior-facing cameras of the HMD and determine a brightness value based on the set of images. In response to a determination that the brightness value is below a brightness threshold, some embodiments may initiate a testing operation that includes one or more operations described by blocks 508, 512, 532, etc.

In some embodiments, the HMD may be configured to wait for an audio stimulus and initiate a testing operation in response to receiving the audio stimulus. The audio stimulus may be received with a microphone of the HMD, and may require that the stimulus be received as a specific type of sound or sequence of sounds. Alternatively, or in addition, some embodiments may treat the audio stimulus as a voice-activated stimulus and determine whether the audio stimulus satisfies one or more voice-related criteria. For example, some embodiments may determine whether a natural language processing application outputs a specific word or a specific set of words when provided with the audio stimulus, whether the audio stimulus is provided by a specific user's voice, etc. After receiving the audio stimulus and determining that the audio stimulus satisfies one or more associated audio stimulus criteria, some embodiments may initiate one or more operations described in this disclosure, such as an operation described by block 508, block 512, block 532, etc.

Some embodiments may collect eye-related readings with a set of cameras or other sensors of the HMD, as indicated by block 508. Eye-related readings may include images, such as images collected by a camera. For example, some embodiments may collect eye-related readings within a set of interior-facing cameras. In some embodiments, the HMD may collect other types of eye-related readings, such as reflectometry measurements, ellipsometry measurements, etc. When collecting readings, some embodiments may collect readings in a sequence, such as collecting a video of an eye over a duration.

In some embodiments, the HMD may present visual stimuli to an eye, where the visual stimuli may cause the eye to change its gaze to focus on the visual stimulus. Some embodiments may collect eye-related readings during the presentation of a sequence of visual stimuli. For example, some embodiments may present a sequence of dots on a lens of the HMD over a 30-second duration and collect images of the eye with an interior-facing camera during this 30-second duration. Some embodiments may obtain a respective set of images of an eye when each respective stimulus of the sequence of visual stimuli is displayed on the HMD lens. Some embodiments may then use this information to derive a gaze location of the eye and other types of eye-related information, as described elsewhere in this disclosure. For example, some embodiments may determine a respective gaze location for each respective stimulus that is presented on the HMD lens. Some embodiments may activate a bleaching light in response to a determination that a gaze location is focused on a target region. For example, some embodiments may set the respective target region for a respective stimulus to be within a threshold range of a presentation location of a respective stimulus, where the threshold range may represent a linear distance, an angular distance, etc.

Some embodiments may determine a pupil size or other additional eye-related information based on the set of eye-related readings, as indicated by block 512. Some embodiments may use eye-related readings to determine additional eye-related information. The additional eye-related information may include information such as whether an eye is open or closed, a percentage representing the degree to which an eye is open, a pupil size, an eye color, an eye orientation, other descriptors of the eye, a health condition related to the eye, a health condition of the person having the eye, etc.

Some embodiments may determine eye-related information by using a set of classifiers of an application executed by an HMD. For example, some embodiments may perform operations to detect image regions indicating the presence of eyes by providing an image to a set of classifiers. Some embodiments may then use a second set of classifiers or another set of implemented algorithms to determine a pupil size based on the pixels of the image regions. For example, some embodiments may perform edge detection method operations to first draw a set of boundaries for an image of an eye and components of the eye within an image region. Some embodiments may then determine a pupil size based on the set of drawn boundaries. As described elsewhere in this disclosure, some embodiments may then determine whether the pupil size satisfies a threshold and, in response to a determination that the pupil size satisfies a threshold, send a message to an attachment device using a transmitter of the HMD.

Some embodiments may determine whether a set of light-activating criteria is satisfied based on the pupil size or additional eye-related information, as indicated by block 532. Some embodiments may wait until the set of light-activating criteria is satisfied before sending a set of messages to an attachment device that causes the attachment device to emit a bleaching light. Alternatively, or additionally, the set of light-activating criteria may be divided into subsets of criteria, such that the satisfaction of different subsets may cause the transmission of different sets of messages. For example, some embodiments may send a first set of messages to the attachment device based on a determination that a first subset of criteria is satisfied and send a second set of messages to the attachment device based on a determination that a second subset of criteria is satisfied.

In some embodiments, the set of light-activating criteria may include a criterion that a pupil size is greater than a minimum threshold, where a minimum threshold may include values less than or equal to 10 mm, values less than or equal to 5 mm, values less than or equal to 3 mm, values less than or equal to 1 mm, etc. For example, the minimum threshold may be equal to 5 mm, where some embodiments may determine that the set of light-activating criteria is satisfied if a determined pupil size is greater than 5 mm. Alternatively, the minimum threshold may be equal to 4 mm, where some embodiments may determine that the set of light-activating criteria is satisfied if the determined pupil size is greater than 4 mm.

In some embodiments, the set of light-activating criteria may include multiple criterion that must each be satisfied in order for a set of light-activating messages to be transmitted by an HMD. For example, some embodiments may use a set of criteria that include a first criterion that a pupil size be greater than 4 mm and a second criterion that a gaze location for the eye be focused on a specific display location of the HMD. Some embodiments may then transmit a set of light-activating messages based on a determination that both the first criterion and the second criterion are satisfied. Though the above example discloses a set of light-activating criteria having two criteria, other number of criteria are possible for inclusion in the set of light-activating criteria.

If the set of light-activating criteria is satisfied by the pupil size or other eye-related information, operations of the process 500 may proceed to operations described by block 540. Otherwise, operations of the process 500 may return to operations described by block 504.

Some embodiments may transmit a set of messages to an attachment, as indicated by block 540. Some embodiments may wirelessly transmit a set of messages via a communication protocol such as Bluetooth, 2.4 GHz Wi-Fi, 5.0 GHz Wi-Fi, or some other wireless communication protocol. In some embodiments, the set of wireless messages may be the same as other set of wireless messages transmitted from the HMD to an attachment device. For example, in response to a determination that a threshold amount of an eye is open at a first time point, some embodiments may send a first set of messages that causes the attachment device to emit a bleaching light. Some embodiments may then send the same set of messages to the attachment device in response to a determination that the threshold amount is satisfied at a second timepoint.

Alternatively, some embodiments may send different sets of messages based on which subset of criteria is satisfied by eye-related information. For example, some embodiments may determine a first pupil size based on a first set of eye-related readings and determine that the first pupil size is less than a size threshold. Based on a determination that the first pupil size is less than the first threshold, some embodiments may generate or update a first set of messages to include a first value for a parameter field. Some embodiments may then send the first set of messages to an attachment device, where the first value for the parameter field may cause the attachment device to emit a first bleaching light at a first intensity for a first duration. Some embodiments may then determine a second pupil size based on a second set of eye-related readings and determine that the second pupil size is greater than the size threshold. Based on a determination that the pupil size is greater than the size threshold, some embodiments may generate or update a second set of messages to include a second value that causes the attachment device to emit a second bleaching light having a lesser intensity than the first bleaching light. Some embodiments may modify the duration instead of the intensity of a bleaching light based on messages sent by the HMD. Alternatively, some embodiments may modify both a duration and intensity of a light emitted by the attachment device based on a set of messages sent from the HMD.

Some embodiments may determine a parameter value used to control LED operations based on a set of user-provided values. For example, some embodiments may receive a user-provided value indicating that a bleaching time was too uncomfortable, where the user-provided value may be provided via the user interacting with a physical button, interacting with a display on the HMD, providing a verbal input, etc. In response to receiving the user-provided value, some embodiments may update a configuration parameter and then generate a new message based on the configuration parameter to include a parameter value that controls a duration or intensity of light emission by a set of LEDs. For example, a user may press a button that updates a configuration parameter used to determine a light emission intensity. In response to receiving the user-provided value, some embodiments may reduce a value for the configuration parameter by 1, such as by reducing the value for the configuration parameter from "1.00" to "0.90," where the value represents a normalized intensity. Some embodiments may then generate a new message that includes the configuration parameter "0.90," where the value of the configuration parameter may cause an attachment device to emit light with a set of LEDs with an intensity equal to 90% of the maximum intensity of the set of LEDs.

Some embodiments may determine which parameter values to use for a set of messages used to activate a set of LEDs based on a selection of a test category, where the test category may represent different types of test configurations. For example, some embodiments may receive a first user-selected input indicating the selection of a first dark adaptation testing operation. Some embodiments may then send a first set of messages to an attachment, with the first set of messages includes parameters that causes the attachment to activate a first LED subset of LEDs. Some embodiments may then receive a second user-selected input indicating the selection of a second dark adaptation testing operation. Some embodiments may then send a second set of messages to the attachment, where the second set of messages includes parameters that causes the attachment to activate a second LED subset of LEDs that are different from the first set of LEDs. In some embodiments, the first and second LED subsets may emit light at different wavelengths. For example, the first LED subset may emit light at wavelengths centered around 480 nanometers (nm) and the second LED subset may emit light at frequencies centered around 520 nm. By causing the selection of different subsets of LEDs to be activated, some embodiments may perform specific types of bleaching that do not require total bleaching of the photoreceptors of an eye.

Some embodiments may activate a set of LEDs of the attachment in response to receiving the set of messages, as indicated by block 544. As described elsewhere in this disclosure, the set of LEDs may be a part of an accessory or attachment to an HMD, where a circuitry of the accessory or other attachment to an HMD may control the set of LEDs. In some embodiments, circuitry of an attachment may receive the set of messages sent by the HMD via a wireless receiver of the circuitry, where the circuitry stores program instructions to control a set of LEDs based on the received set of messages. Once activated, the set of LEDs may emit light at various intensities including a bleaching intensity, where the emitted light may pass through a transparent lens of the HMD.

Some embodiments may receive different parameter values when receiving different sets of messages to activate one or more LEDs. For example, a circuitry of an attachment may configure an intensity of the light emitted by a set of LEDs based on a parameter value communicated via a received message sent from an HMD. Alternatively, or additionally, the circuitry may configure a duration for the light being emitted. As described elsewhere, the parameter value may be determined by an HMD based on various types of values, such as eye-related readings, other associated eye-related information, user-provided values, etc.

As described elsewhere, an attachment may include a first and second circuitry, where a first circuitry may control a set of LEDs based on received messages, and where the second circuitry may deactivate the set of LEDs if a set of safety criteria is satisfied. In some embodiments, the second circuitry may deactivate the set of LEDs and send a warning message to the HMD indicating that the second circuitry has deactivated the set of LEDs if the set of LEDs were configured by a message to emit light for longer than a duration threshold of the second circuitry. In some embodiments, the warning message may indicate that the configured duration exceeds the duration threshold, where the application executing on the HMD may search through a set of configuration parameters used to set or otherwise update LED emission durations. The HMD may then select a subset of the set of configuration parameters used to control LED emission durations, where the selected subset exceeds a duration threshold of the second circuitry. Some embodiments may then visually indicate this subset of configuration parameters for a user to update or delete. Alternatively, some embodiments may automatically update the values of this subset of configuration parameters such that none of the updated configuration parameters will cause the set of LEDs to exceed the safety duration threshold.

As described elsewhere, some embodiments may collect eye-related readings when the set of LEDs are emitting light. For example, a set of interior-facing cameras of the HMD may collect eye-related readings with a camera during a data collection period, where the set of LEDs may emit bleaching light concurrently with the data collection period. The HMD may determine a set of eye-related information based on the collected readings during the first data collection period and determine whether the eye-related information satisfies a set of criteria.

Some embodiments may use readings collected during and after a first data collection period to determine whether to activate a set of LEDs, collect eye-related readings, or perform other operations for a second data collection period. For example, after collecting eye-related readings, some embodiments may collect images of an eye during a first data collection period and determine an associated set of eye-related information indicating an eye pigment recovery rate after an eye is exposed to bleaching light. Some embodiments may then determine whether the recovery rate satisfies a recovery rate threshold, where the recovery rate threshold may be a type of time-based criterion. The set of time-based criteria may include various types of criteria, such as a criterion that a rate is greater than or equal to a minimum rate, a rate is less than or equal to a maximum rate, that a total change in a set of measurements or derived value based on the set of measurements satisfies a change threshold, etc. For example, satisfying the set of time-based criteria may include determining a rate of rhodopsin regeneration, rate of cone pigment regeneration, or rate of melanopsin regeneration based on sensor readings collected by the HMD and determining whether the rate is greater than a minimum rate. Alternatively, or additionally, the rate may include a rate of change in a pupil size or other adjustment mechanisms of an eye. In response to a determination that the set of time-based criteria is not satisfied, some embodiments may then initiate a second testing operation to emit light with the set of LEDs of an attachment and collect a second set of eye-related readings during a second data collection period. In some embodiments, the HMD may determine whether the set of time-based criteria is satisfied based on the second set of eye-related readings. In response to a determination that the second set of eye-related readings satisfies the set of time-based criteria, some embodiments may store the readings and information derived from the readings in a persistent memory of the HMD or another computer device.

It should be noted that the features and limitations described in any one embodiment may be applied to any other embodiment herein, and a flowchart or examples relating to one embodiment may be combined with any other embodiment in a suitable manner, done in different orders, or done in parallel. In addition, the systems and methods described herein may be performed in real time. It should also be noted that the systems and/or methods described above may be applied to, or used in accordance with, other systems and/or methods.

Figure 6:
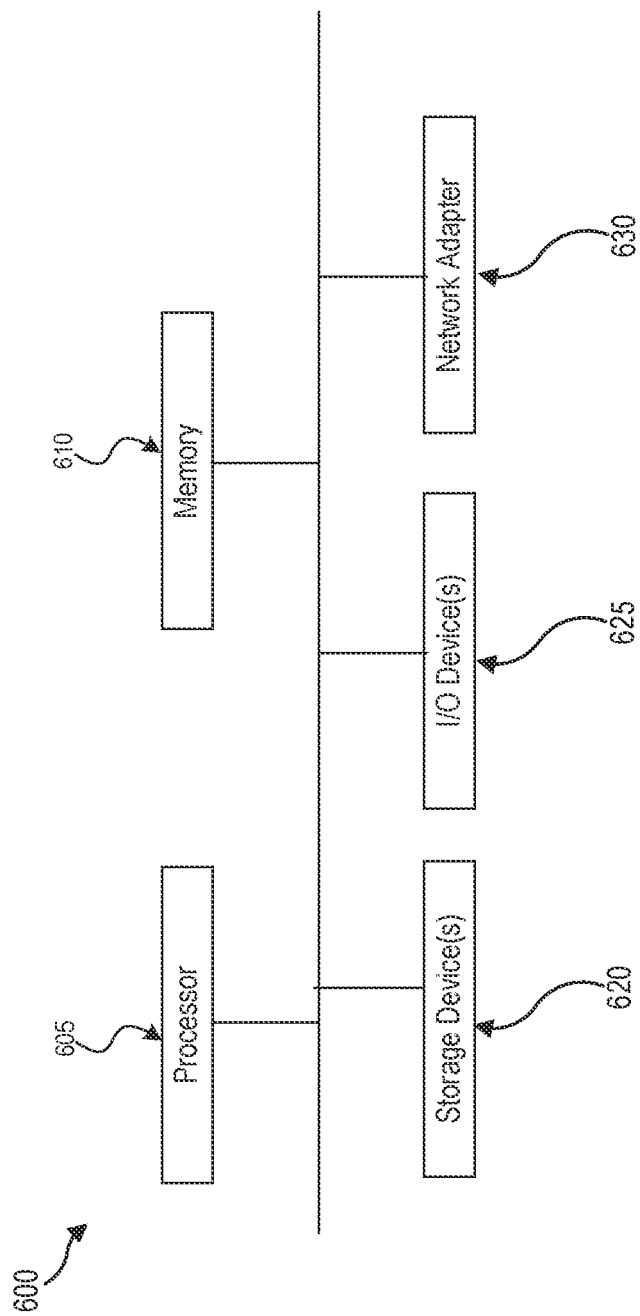
FIG. 6 is a block diagram of a computer system as may be used to implement certain features of some of the embodiments.

FIG. 6 is a block diagram of a computer system as may be used to implement certain features of some of the embodiments. The computer system 600 may include a set of central processing units ("set of processors") 605, memory 610, input/output devices 625, e.g., keyboard and pointing devices, touch devices, display devices, storage devices 620, e.g., disk drives, and network adapters 630, e.g., network interfaces, that are connected to an interconnect 615. The interconnect 615 is illustrated as an abstraction that represents any one or more separate physical buses, point-to-point connections, or both connected by appropriate bridges, adapters, or controllers. The interconnect 615, therefore, may include, for example, a system bus, a Peripheral Component Interconnect (PCI) bus or PCI-Express bus, a HyperTransport or industry standard architecture (ISA) bus, a small computer system interface (SCSI) bus, a universal serial bus (USB), an IIC (I2C) bus, or an Institute of Electrical and Electronics Engineers (IEEE) standard 1394 bus, also called FireWire.

The memory 610 and storage devices 620 are computer-readable storage media that may store program instructions that implement at least portions of the various embodiments. In addition, the data structures and message structures may be stored or transmitted via a data transmission medium, e.g., a signal on a communications link. Various communications links may be used, e.g., the Internet, a local area network, a wide area network, or a point-to-point dial-up connection. Thus, computer-readable media can include computer-readable storage media, e.g., non-transitory media, and computer-readable transmission media.

In some embodiments, software or firmware may be initially provided to the computer system 600 by downloading it from a remote system through the computer system 600, e.g., via network adapter 630. The provided software or firmware may be stored in memory 610. The program instructions stored in memory 610 can be implemented as software and/or firmware to program the set of processors 605 to carry out actions described above. For example, some embodiments may use the set of processors 605 to determine a set of decision parameters using a neural network model or another type of machine learning model.

The various embodiments introduced herein can be implemented by, for example, programmable circuitry, e.g., one or more microprocessors, programmed with software and/or firmware, or entirely in special purpose hardwired (non-programmable) circuitry, or in a combination of such forms. Special-purpose hardwired circuitry may be in the form of, for example, one or more ASICs, PLDs, FPGAs, etc.

With respect to the components of computer devices described in this disclosure, each of these devices may receive content and data via input/output (hereinafter "I/O") paths. Each of these devices may also include processors and/or control circuitry to send and receive commands, requests, and other suitable data using the I/O paths. The control circuitry may comprise any suitable processing, storage, and/or input/output circuitry. Further, some or all of the computer devices described in this disclosure may include a user input interface and/or user output interface (e.g., a display) for use in receiving and displaying data. In some embodiments, a display such as a touchscreen may also act as a user input interface. It should be noted that in some embodiments, one or more devices described in this disclosure may have neither user input interfaces nor displays and may instead receive and display content using another device (e.g., a dedicated display device such as a computer screen and/or a dedicated input device such as a remote control, mouse, voice input, etc.). Additionally, one or more of the devices described in this disclosure may run an application (or another suitable program) that performs one or more operations described in this disclosure.

Although the present invention has been described in detail for the purpose of illustration based on what is currently considered to be the most practical and preferred embodiments, it is to be understood that such detail is solely for that purpose and that the invention is not limited to the disclosed embodiments, but, on the contrary, is intended to cover modifications and equivalent arrangements that are within the scope of the appended claims. For example, it is to be understood that the present invention contemplates that, to the extent possible, one or more features of any embodiment may be combined with one or more features of any other embodiment.

As used throughout this application, the word "may" is used in a permissive sense (i.e., meaning having the potential to), rather than the mandatory sense (i.e., meaning must). The words "include," "including," "includes," and the like mean including, but not limited to. As used throughout this application, the singular forms "a," "an," and "the" include plural referents unless the context clearly indicates otherwise. Thus, for example, reference to "an element" or "an element" includes a combination of two or more elements, notwithstanding use of other terms and phrases for one or more elements, such as "one or more." The term "or" is non-exclusive (i.e., encompassing both "and" and "or"), unless the context clearly indicates otherwise. Terms describing conditional relationships (e.g., "in response to X, Y," "upon X, Y," "if X, Y," "when X, Y," and the like) encompass causal relationships in which the antecedent is a necessary causal condition, the antecedent is a sufficient causal condition, or the antecedent is a contributory causal condition of the consequent (e.g., "state X occurs upon condition Y obtaining" is generic to "X occurs solely upon Y" and "X occurs upon Y and Z"). Such conditional relationships are not limited to consequences that instantly follow the antecedent obtaining, as some consequences may be delayed, and in conditional statements, antecedents are connected to their consequents (e.g., the antecedent is relevant to the likelihood of the consequent occurring). Statements in which a plurality of attributes or functions are mapped to a plurality of objects (e.g., one or more processors performing steps/operations A, B, C, and D) encompass both all such attributes or functions being mapped to all such objects and subsets of the attributes or functions being mapped to subsets of the objects (e.g., both all processors each performing steps/operations A-D, and a case in which processor 1 performs step/operation A, processor 2 performs step/operation B and part of step/operation C, and processor 3 performs part of step/operation C and step/operation D), unless otherwise indicated. Further, unless otherwise indicated, statements that one value or action is "based on" another condition or value encompass both instances in which the condition or value is the sole factor and instances in which the condition or value is one factor among a plurality of factors.

Unless the context clearly indicates otherwise, statements that "each" instance of some collection have some property should not be read to exclude cases where some otherwise identical or similar members of a larger collection do not have the property (i.e., each does not necessarily mean each and every). Limitations as to sequence of recited steps should not be read into the claims unless explicitly specified (e.g., with explicit language like "after performing X, performing Y"), in contrast to statements that might be improperly argued to imply sequence limitations (e.g., "performing X on items, performing Y on the X' ed items") used for purposes of making claims more readable rather than specifying sequence. Statements referring to "at least Z of A, B, and C" and the like (e.g., "at least Z of A, B, or C") refer to at least Z of the listed categories (A, B, and C) and do not require at least Z units in each category. Unless the context clearly indicates otherwise, it is appreciated that throughout this specification discussions utilizing terms such as "processing," "computing," "calculating," "determining," or the like refer to actions or processes of a specific apparatus, such as a special purpose computer or a similar special purpose electronic processing/computing device. Furthermore, unless indicated otherwise, updating an item may include generating the item or modifying an existing time. Thus, updating a record may include generating a record or modifying the value of an already-generated value.

ENUMERATED EMBODIMENTS

The present techniques will be better understood with reference to the following enumerated embodiments:

A.1. A system comprising: a head-mounted display comprising transparent lenses and exterior-facing cameras on a front end of the head-mounted display and adjacent to the transparent lenses, wherein at least one pair of cameras of the exterior-facing cameras are on opposite sides of a vertical plane of the head-mounted display; and an accessory device positioned on a front end of the head-mounted display, the accessory device comprising: a light shield casing comprising: a cavity that encompasses the transparent lenses of the head-mounted display when the accessory device is attached to the head-mounted display, wherein the light shield casing shields the cavity from light from an environment of the head-mounted display when the accessory device is attached to the head-mounted display; and a plurality of apertures aligned with the exterior-facing cameras; and an attachment body fixed to a front end of the light shield casing, the attachment body comprising: a set of light-emitting diodes (LEDs) to emit light at a bleaching intensity, wherein the set of LEDs is attached to a back end of the attachment body and is directed towards at least one lens of the transparent lens, and wherein light emitted by the set of LEDs is visible through at least one lens of the transparent lenses; and a circuitry that is at least partially enclosed within the attachment body and is in electrical communication with the set of LEDs, wherein the circuitry is configured to control the light emission of the set of LEDs.

A.2. The system of embodiment A.3, wherein the circuitry is a controller circuitry, and wherein the attachment body further comprises a safety circuitry that is in electrical communication with the set of LEDs, wherein the safety circuitry comprises a relay or microcontroller to deactivate the set of light-emitting diodes independently of the controller circuitry.

A.3. The system of any of embodiments A.1 to A.2, wherein the controller circuitry is configured to perform operations comprising: emitting a first light at a first intensity with the set of LEDs in response to receiving a first command via an interface of the circuitry, wherein the first intensity is not a bleaching intensity; and emitting a second light at a second intensity with the set of LEDs in response to receiving a second command via the interface, wherein the second intensity is a bleaching intensity.

A.4. The system of any of embodiments A.1 to A.3, wherein the circuitry performs operations comprising emitting a first light at a first intensity with the set of LEDs in response to receiving a first command via an interface of the circuitry, wherein the first light is emitted concurrently with a light emitted by the head-mounted display.

A.5. The system of any of embodiments A.1 to A.4, further comprising: a filter coupling; and a neutral density filter fixed to the filter coupling, wherein the set of LEDs is directed towards the neutral density filter such that the light emitted by the set of LEDs passes through the neutral density filter.

A.6. The system of any of embodiments A.1 to A.5, wherein the plurality of apertures comprises at least six apertures, and wherein at least one aperture of the plurality of apertures is aligned with a microphone.

A.7. A device comprising: a casing comprising a cavity, wherein a lens of a head-mounted display is positioned inside the cavity when the device is attached to the head-mounted display, and wherein an aperture of the casing is aligned with an exterior-facing camera of the head-mounted display; and an attachment body, wherein a posterior end of the attachment body is fixed to an anterior end of the casing, the attachment body comprising: a set of light-emitting diodes (LEDs), wherein the set of LEDs is attached to the posterior end of the attachment body and is directed towards the lens; and a circuitry that is configured to control light emission of the set of LEDs.

A.8. The device of embodiment A.7, wherein: the lens is a first lens; the attachment body comprises a midsection that is bisected by a sagittal plane of the attachment body; the midsection is longer along the sagittal plane of the attachment body in comparison to a left section of the attachment body or a right section of the attachment body; the set of LEDs is a first set of LEDs; a second set of LEDs is attached to the posterior end of the attachment body and is directed towards a second lens of the head-mounted display; the first set of LEDs and the second set of LEDs are substantially symmetric about the sagittal plane; and a distance between the first set of LEDs and the second set of LEDs is greater than or equal to 40 millimeters.

A.9. The device of any of embodiments A.7 to A.8, wherein the circuitry is a first circuitry, and wherein a second circuitry comprises a microcontroller configured to perform operations comprising: determining whether a power consumption of the set of LEDs satisfies a power threshold; in response to a determination that the power consumption of the set of LEDs satisfies the power threshold, determining whether a light emission duration of the set of LEDs satisfies a duration threshold; and deactivating the set of LEDs in response to a determination that the light emission duration satisfies the duration threshold.

A.10. The device of any of embodiments A.7 to A.9, wherein the set of LEDs is positioned below a transverse plane of the attachment body.

A.11. The device of any of embodiments A.7 to A.10, wherein the attachment body is fixed to the casing at a plurality of attachment positions.

A.12. The device of any of embodiments A.7 to A.11, wherein the attachment body is fixed to the casing by at least one of a threaded member, a snap fastener member, or an adhesive.

A.13. The device of any of embodiments A.7 to A.13, wherein: the aperture is a first aperture; the casing comprises a plurality of apertures; the plurality of apertures is greater than three apertures; each respective aperture of the plurality of apertures is aligned with at least one sensor of a plurality of sensors of the head-mounted display.

A.14. A device comprising: a casing comprising a cavity, wherein a lens of a head-mounted display is positioned inside the cavity when the device is attached to the head-mounted display; and an attachment body, wherein a posterior end of the attachment is fixed to an anterior end of the casing, the attachment body comprising: a set of light-emitting diodes (LEDs), wherein the set of LEDs is attached to the posterior end of the attachment body and is directed towards the anterior end of the casing; a first circuitry that is configured to control light emission of the set of LEDs; and a second circuitry that is in electrical communication with the set of LEDs, wherein the second circuitry is configured to deactivate the set of LEDs independently of the first circuitry.

A.15. The device of embodiment A.14, wherein the second circuitry is configured to deactivate the set of LEDs in response to the set of LEDs being activated for a duration threshold.

A.16. The device of any of embodiments A.14 to A.15, wherein: the attachment body comprises an antenna; the first circuitry is in communication with the antenna; and the second circuitry is not in communication with the antenna.

A.17. The device of embodiment A.16, wherein the first circuitry comprises: a memory; and a set of processors, wherein the memory stores program instructions that, when executed by the set of processors, cause the set of processors to perform operations comprising: detecting that the second circuitry has deactivated the set of LEDs; and sending a wireless message to a computing device indicating that the second circuitry has deactivated the set of LEDs.

A.18. The device of any of embodiments A.14 to A.17, wherein the set of LEDs is configured to emit bleaching light on a retinal surface area such that at least one arc of a region illuminated by the bleaching light is greater than two degrees.

A.19. The device of any of embodiments A.14 to A.18, wherein: the set of LEDs is a first set of LEDs; a second set of LEDs is directed to a second lens of the head-mounted display; and the attachment body comprises a third circuitry that is in electrical communication with the second set of LEDs, wherein the second circuitry is configured to deactivate the set of LEDs independently of the first circuitry and the second circuitry.

A.20. The device of embodiment A.20, wherein the set of LEDs is movable along a horizontal direction of the attachment body or vertical direction of the attachment body.

B.1. A system comprising: an attachment body fixed to an anterior end of a casing by a coupling, the attachment body comprising: a set of light-emitting diodes (LEDs), wherein the set of LEDs is attached to posterior end of the attachment body and is directed towards the anterior end of the casing; and a circuitry, the circuitry comprising a first sub-circuitry and a second sub-circuitry, wherein the first sub-circuitry is configured to control light emission of the set of LEDs, and wherein the second sub-circuitry is configured to deactivate the set of LEDs independently of the first sub-circuitry; a set of processors; and a memory storing program instructions that, when executed by the set of processors, causes the set of processors to perform operations comprising: emitting light at a target intensity using the set of light-emitting diodes (LEDs); and receiving measurements of eye responses from a head-mounted display after the emission of the light at the target intensity.

B.2. The system of embodiment B.1, the operations further comprising: detecting that the set of LEDs has stopped emitting the light at the target intensity; and receiving, from the circuitry, a signal indicating the light at the target intensity is not being emitted within 5 milliseconds after detecting that the set of LEDs have stopped emitting the light at the target intensity.

B.3. The system of any of embodiments B.1 to B.2, the operations further comprising: obtaining a retina position based on a measurement of the eye; selecting the set of LEDs by determining an illumination position that will center light within a first degree range of the eye, wherein emitting the light at the target intensity comprises illuminating a retinal surface area such that at least one arc of the retinal surface area is greater than two degrees.

B.4. The system of any of embodiments B.1 to B.3, the operations further comprising: determining a pupil radius based on the measurements of eye responses; determining a target brightness based on the pupil radius, wherein the target brightness is negatively correlated with the pupil radius; updating a brightness of a stimulus displayed on a lens of the head-mounted display with the target brightness.

B.5. The system of any of embodiments B.1 to B.4, wherein: the set of LEDs is a first set of LEDs; a second set of LEDs is directed to a second lens of the head-mounted display; and emitting the light at the target intensity comprises emitting the light using the first set of LEDs without emitting light using the second set of LEDs.

C.1. A system comprising: an HMD comprising a transparent lens and a memory storing program instructions that, when executed by a set of processors of the HMD, performs operations comprising: determining whether a set of light-activating criteria is satisfied based on a set of images collected by an interior-facing camera of the HMD by detecting image regions indicating a human eye based on the set of images; and wirelessly transmitting a set of activating messages in response to a determination that the set of light-activating criteria is satisfied; and an accessory configured to attach to the HMD and comprising a set of light-emitting diodes (LEDs) to emit a bleaching light having a bleaching intensity that is visible through the transparent lens of the HMD, wherein a circuitry of the accessory stores program instructions that, when executed by the circuitry, performs operations comprising: receiving the set of activating messages via a wireless receiver of the accessory; and in response to receiving the set of activating messages, activating the set of LEDs to emit the light at the bleaching intensity through the transparent lens of the HMD.

C.2. The system of any of embodiments C.1 to C.2, wherein: the HMD comprises exterior-facing cameras on a front end of the HMD; and the accessory comprises: a casing comprising a cavity that encompasses the transparent lens of the HMD when the casing is attached to the HMD, wherein a plurality of apertures are aligned with the exterior-facing cameras of the HMD when the casing is attached to the HMD; and an accessory body, wherein a back end of the accessory body is fixed to a front end of the casing, wherein: the set of LEDs is attached to a back end of the accessory body and is directed towards the transparent lens; the circuitry is at least partially enclosed within the accessory body; and the circuitry comprises the wireless receiver.

C.3. A system comprising: a head-mounted display (HMD) comprising a memory storing program instructions that, when executed by a set of processors of the HMD, performs operations comprising: determining whether a set of criteria is satisfied based on eye-related readings collected by a camera the HMD; and wirelessly transmitting a set of messages in response to a determination that the set of criteria is satisfied; and an attachment comprising a set of light-emitting diodes (LEDs) to emit a light at a bleaching intensity that passes through a lens of the HMD, wherein the attachment stores program instructions that, when executed by the attachment, performs operations comprising activating the set of LEDs to emit the light at the bleaching intensity in response to receiving the set of messages.

C.4. The system of embodiment C.3, wherein: the eye-related readings comprises a set of images; and determining whether the set of criteria is satisfied comprises: detecting an eye of the set of images; determining a gaze location of the eye based on the set of images; determining that the gaze location of the eye is focused in a target region, wherein determining that the set of criteria is satisfied comprises determining that the gaze location is focused in the target region.

C.5. The system of any of embodiments C.3 to C.4, wherein: the eye-related readings are first eye-related readings; the set of messages is a first set of messages; and the operations further comprising: determining a first pupil size based on the first eye-related readings; generating or updating the first set of messages to comprise a first set of parameter that causes the set of LEDs to emit light at a first brightness based on a determination that the first pupil size is less than a size threshold; obtaining second eye-related readings via the camera; determining a second pupil size based on the second eye-related readings; generating or updating a second set of messages to comprise a second set of parameters that causes the set of LEDs to emit light at a second brightness based on a determination that the second pupil size is greater than the size threshold, wherein the second brightness is less than the first brightness; and transmitting the second set of messages to the attachment.

C.6. The system of embodiment C.5, wherein the size threshold is less than or equal to 5 millimeters.

C.7. The system of any of embodiments C.3 to C.6, wherein the set of messages is a first set of messages, the operations further comprising: determining a pupil size based on the eye-related readings; generating or updating the first set of messages to comprise information that causes the set of LEDs to emit light at a first brightness based on a determination that the pupil size is less than a size threshold; receiving, with the HMD, a user-provided value indicating that a brightness was too long; adjusting a configuration parameter; and generating or updating a second set of messages based on the configuration parameter, wherein the second set of messages causes the set of LEDs to emit light at a second brightness that is less than the first brightness.

C.8. The system of any of embodiments C.3 to C.7, wherein: the set of messages causes the attachment to determine a luminosity; and the attachment stores program instructions to determine a current based on the luminosity.

C.9. The system of any of embodiments C.3 to C.8, the operations further comprising receiving a voice-activated stimulus, wherein determining whether the set of criteria is satisfied comprises initiating a testing operation that causes the attachment to determine whether the set of criteria is satisfied in response to receiving the voice-activated stimulus.

C.10. The system of any of embodiments C.3 to C.9, the operations further comprising: receiving a set of images based on a set of exterior-facing cameras of the HMD; detected a target motion or a target shape based on the set of images; and determining whether a set of visual stimulus criteria is satisfied based on the target motion or the target shape, wherein determining whether the set of criteria is satisfied comprises initiating a testing operation that causes the attachment to determine whether the set of criteria is satisfied in response to determining that the set of visual stimulus criteria is satisfied.

C.11. The system of any of embodiments C.3 to C.10, wherein: the eye-related readings comprises a set of images; and determining whether the set of criteria is satisfied comprises: detecting an image region indicating an eye by providing the set of images to a set of classifiers; determining a pupil size of the eye based on the image region; determining whether the pupil size satisfies a minimum threshold, wherein determining that the set of criteria is satisfied comprises determining that the pupil size satisfies the minimum threshold.

C.12. A method comprising: determining, with a head-mounted display (HMD), whether a set of criteria is satisfied based on eye-related readings collected by a sensor the HMD; wirelessly transmitting, with the HMD, a set of messages in response to a determination that the set of criteria is satisfied; and activating, with an attachment, a set of LEDs of the attachment to emit a bleaching light that passes through a lens of the HMD in response to receiving the set of messages.

C.13. The method of embodiment C.12, wherein activating the set of LEDs comprises activating the set of LEDs using a first circuitry of the attachment, further comprising: deactivating, with a second circuitry of the attachment, the set of LEDs in response to the set of LEDs being activated for a duration threshold, wherein the first circuitry is different from the second circuitry; and sending a warning message to the HMD indicating that the second circuitry has deactivated the set of LEDs.

C.14. The method of any of embodiments C.12 to C.13, further comprising: retrieving, from a memory of the HMD, configuration parameters that sets or updates LED emission durations; determining a subset of the configuration parameters associated with LED emission durations that exceed a duration threshold; and visually indicating the subset of the configuration parameters on a display device.

C.15. The method of any of embodiments C.12 to C.14, further comprising: displaying a visual stimulus on the lens; determining a gaze location based on the eye-related readings; and determining whether the gaze location is within a threshold range of the visual stimulus, wherein transmitting the set of messages comprises transmitting the set of messages in response to a determination that the gaze location is within the threshold range of the visual stimulus.

C.16. The method of embodiment C.15, wherein the visual stimulus is a first visual stimulus, the gaze location is a first gaze location, further comprising: displaying a sequence of visual stimuli on the lens, wherein the sequence of visual stimuli comprises the first visual stimulus; and for each respective stimulus of the sequence of visual stimuli: obtaining a respective set of images of an eye with the sensor; determining a respective gaze location based on the respective set of images; determining whether the respective gaze location is within a respective threshold range of the respective stimulus; and activating the set of LEDs in response to a determination that the respective gaze location is within the respective threshold range of the respective stimulus.

C.17. The method of any of embodiments C.12 to C.16, wherein activating the set of LEDs comprises activating the set of LEDs during a first duration, further comprising: collecting a set of eye-related readings with the sensor during a data collection period after the set of LEDs is activated; determining a set of eye-related information based on the set of eye-related readings, wherein the set of eye-related information indicates values over the data collection period; determining, with the HMD, whether a set of time-based criteria is satisfied based on the set of eye-related information; and transmitting a second set of messages to a receiver of the attachment that causes the set of LEDs to emit light during a second duration based on a determination that the set of time-based criteria is not satisfied.

C.18. The method of embodiment C.17, wherein the eye-related readings is a first set of eye-related readings, further comprising: collecting second eye-related readings with the sensor during a second data collection period after the second duration; determining a second set of eye-related information based on the second eye-related readings, wherein the second set of eye-related information indicates changes over the second data collection period; determining, with the HMD, whether the set of time-based criteria is satisfied based on the second set of eye-related information; and presenting a visual stimulus on the lens in response to a determination that the set of time-based criteria is satisfied.

C.19. The method of any of embodiments C.12 to C.18, further comprising obtaining, with the HMD, a test category indicating a test configuration, wherein transmitting the set of messages comprises transmitting parameters indicating an LED subset of the set of LEDs to activate based on the test category.

C.20. The method of embodiment C.19, wherein the LED subset of the set of LEDs emit light at a first wavelength that is different a second wavelength emitted by an LED of the set of LEDs not included in the LED subset.

What is claimed is:

1. A head-mounted display and accessory system in which the accessory emits bleaching light through the head-mounted display to bleach photoreceptors for dark adaptation testing, the system comprising:
    a head-mounted display comprising transparent lenses and exterior-facing cameras on a front end of the head-mounted display and adjacent to the transparent lenses, wherein at least one pair of cameras of the exterior-facing cameras are on opposite sides of a vertical plane of the head-mounted display; and
    an accessory device positioned on a front end of the head-mounted display, the accessory device comprising:
        a light shield casing comprising:
            a cavity that encompasses the transparent lenses of the head-mounted display when the accessory device is attached to the head-mounted display, wherein the light shield casing shields the cavity from light from an environment of the head-mounted display when the accessory device is attached to the head-mounted display; and
            a plurality of apertures aligned with the exterior-facing cameras; and
        an attachment body fixed to a front end of the light shield casing, the attachment body comprising:
            a set of light-emitting diodes (LEDs) to emit light at a bleaching intensity, wherein the set of LEDs is attached to a back end of the attachment body and is directed towards at least one lens of the transparent lens, and wherein light emitted by the set of LEDs is visible through at least one lens of the transparent lenses; and
            a circuitry that is at least partially enclosed within the attachment body and is in electrical communication with the set of LEDs, wherein the circuitry is configured to control the light emission of the set of LEDs.

2. The system of claim 1, wherein the circuitry is a controller circuitry, and wherein the attachment body further comprises a safety circuitry that is in electrical communication with the set of LEDs, wherein the safety circuitry comprises a relay or microcontroller to deactivate the set of light-emitting diodes independently of the controller circuitry.

3. The system of claim 1, wherein the controller is configured to perform operations comprising:
    emitting a first light at a first intensity with the set of LEDs in response to receiving a first command via an interface of the circuitry, wherein the first intensity is not a bleaching intensity; and
    emitting a second light at a second intensity with the set of LEDs in response to receiving a second command via the interface, wherein the second intensity is a bleaching intensity.

4. The system of claim 1, wherein the circuitry performs operations comprising emitting a first light at a first intensity with the set of LEDs in response to receiving a first command via an interface of the circuitry, wherein the first light is emitted concurrently with a light emitted by the head-mounted display.

5. The system of claim 1, further comprising:
    a filter coupling; and
    a neutral density filter fixed to the filter coupling, wherein the set of LEDs is directed towards the neutral density filter such that the light emitted by the set of LEDs passes through the neutral density filter.

6. The system of claim 1, wherein the plurality of apertures comprises at least six apertures, and wherein at least one aperture of the plurality of apertures is aligned with a microphone.

7. A device comprising:
    a casing comprising a cavity, wherein a lens of a head-mounted display is positioned inside the cavity when the device is attached to the head-mounted display, and wherein an aperture of the casing is aligned with an exterior-facing camera of the head-mounted display; and
    an attachment body, wherein a posterior end of the attachment body is fixed to an anterior end of the casing, the attachment body comprising:
        a set of light-emitting diodes (LEDs), wherein the set of LEDs is attached to the posterior end of the attachment body and is directed towards the lens; and
        a circuitry that is configured to control light emission of the set of LEDs.

8. The device of claim 7, wherein:
    the lens is a first lens;
    the attachment body comprises a midsection that is bisected by a sagittal plane of the attachment body;
    the midsection is longer along the sagittal plane of the attachment body in comparison to a left section of the attachment body or a right section of the attachment body;
    the set of LEDs is a first set of LEDs;

a second set of LEDs is attached to the posterior end of the attachment body and is directed towards a second lens of the head-mounted display;

the first set of LEDs and the second set of LEDs are substantially symmetric about the sagittal plane; and a distance between the first set of LEDs and the second set of LEDs is greater than or equal to 40 millimeters.

9. The device of claim 7, wherein the circuitry is a first circuitry, and wherein a second circuitry comprises a microcontroller configured to perform operations comprising:

determining whether a power consumption of the set of LEDs satisfies a power threshold;

in response to a determination that the power consumption of the set of LEDs satisfies the power threshold, determining whether a light emission duration of the set of LEDs satisfies a duration threshold; and deactivating the set of LEDs in response to a determination that the light emission duration satisfies the duration threshold.

10. The device of claim 7, wherein the set of LEDs is positioned below a transverse plane of the attachment body.

11. The device of claim 7, wherein the attachment body is fixed to the casing at a plurality of attachment positions.

12. The device of claim 7, wherein the attachment body is fixed to the casing by at least one of a threaded member, a snap fastener member, or an adhesive.

13. The device of claim 7, wherein:

the aperture is a first aperture;

the casing comprises a plurality of apertures;

the plurality of apertures is greater than three apertures;

each respective aperture of the plurality of apertures is aligned with at least one sensor of a plurality of sensors of the head-mounted display.

14. A device comprising:

a casing comprising a cavity, wherein a lens of a head-mounted display is positioned inside the cavity when the device is attached to the head-mounted display; and an attachment body, wherein a posterior end of the attachment is fixed to an anterior end of the casing, the attachment body comprising:

a set of light-emitting diodes (LEDs), wherein the set of LEDs is attached to the posterior end of the attachment body and is directed towards the anterior end of the casing;

a first circuitry that is configured to control light emission of the set of LEDs; and a second circuitry that is in electrical communication with the set of LEDs, wherein the second circuitry is configured to deactivate the set of LEDs independently of the first circuitry.

15. The device of claim 14, wherein the second circuitry is configured to deactivate the set of LEDs in response to the set of LEDs being activated for a duration threshold.

16. The device of claim 14, wherein:

the attachment body comprises an antenna;

the first circuitry is in communication with the antenna; and the second circuitry is not in communication with the antenna.

17. The device of claim 16, wherein the first circuitry comprises:

a memory; and a set of processors, wherein the memory stores program instructions that, when executed by the set of processors, cause the set of processors to perform operations comprising:

detecting that the second circuitry has deactivated the set of LEDs; and sending a wireless message to a computing device indicating that the second circuitry has deactivated the set of LEDs.

18. The device of claim 14, wherein the set of LEDs is configured to emit bleaching light on a retinal surface area such that at least one arc of a region illuminated by the bleaching light is greater than two degrees.

19. The device of claim 14, wherein:

the set of LEDs is a first set of LEDs;

a second set of LEDs is directed to a second lens of the head-mounted display; and the attachment body comprises a third circuitry that is in electrical communication with the second set of LEDs, wherein the second circuitry is configured to deactivate the set of LEDs independently of the first circuitry and the second circuitry.

20. The device of claim 19, wherein the set of LEDs is movable along a horizontal direction of the attachment body or vertical direction of the attachment body.

* * * * *